(12) United States Patent
Wong et al.

(10) Patent No.: US 6,419,952 B2
(45) Date of Patent: Jul. 16, 2002

(54) CONVERSION OF LIQUID FILLED GELATIN CAPSULES INTO CONTROLLED RELEASE SYSTEMS BY MULTIPLE COATINGS

(75) Inventors: Patrick S. -L. Wong, Burlingame; Liang C. Dong, Sunnyvale; Jiansheng Wan, Palo Alto, all of CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 09/866,036

(22) Filed: May 25, 2001

Related U.S. Application Data

(63) Continuation of application No. 09/457,803, filed on Dec. 9, 1999, now abandoned.
(60) Provisional application No. 60/112,634, filed on Dec. 17, 1998.

(51) Int. Cl.[7] .................................................. A61K 9/48
(52) U.S. Cl. .................. 424/463; 424/451; 424/452; 424/453; 424/456; 424/457; 424/468; 424/469; 424/473
(58) Field of Search ................... 424/456, 451, 424/452, 453, 457, 468, 469, 473, 463

(56) References Cited

U.S. PATENT DOCUMENTS

| | | | |
|---|---|---|---|
| 3,995,631 A | | 12/1976 | Higuchi et al. |
| 4,203,440 A | | 5/1980 | Theeuwes |
| 4,327,725 A | | 5/1982 | Cortese et al. |
| 4,612,008 A | | 9/1986 | Wong et al. |
| 4,627,850 A | | 12/1986 | Deters et al. |
| 4,765,989 A | | 8/1988 | Wong et al. |
| 4,783,337 A | | 11/1988 | Wong et al. |
| 5,324,280 A | * | 6/1994 | Wong et al. ............ 604/892.1 |
| 6,027,748 A | | 2/2000 | Conte et al. |

FOREIGN PATENT DOCUMENTS

| | | |
|---|---|---|
| GB | 2148712 | 6/1985 |
| GB | 2182559 | 5/1987 |
| WO | WO9115196 | 10/1991 |

* cited by examiner

Primary Examiner—Thurman K. Page
Assistant Examiner—Liliana Di Nola-Baron
(74) Attorney, Agent, or Firm—Samuel E. Webb

(57) ABSTRACT

A dosage form comprising a gelatin capsule formed with a composite wall and containing a liquid, active agent formulation where the wall comprises a barrier layer formed over the external surface of the gelatin capsule, an expandable layer formed over the barrier layer and a semipermeable layer formed over the expandable layer is described. The dosage forms and methods provide for the conversion of standard gelatin, liquid formulation capsules into controlled, release dosage forms that permit the controlled release of the active agent into the environment of use over time.

20 Claims, 11 Drawing Sheets

CONVERSION OF LIQUID FILLED GELATIN CAPSULES INTO CONTROLLED RELEASE SYSTEMS BY MULTIPLE COATINGS

This application claims the priority of provisional application No. 60/112,634, filed Dec. 17, 1998. This application is a continuation of U.S. patent application Ser. No. 09/457,803, filed Dec. 9, 1999, now abandoned.

FIELD OF THE INVENTION

The invention pertains to a dosage form for delivering liquid, active agent formulations. In particular, it pertains to dosage forms that permit the controlled release of liquid, active agent formulations from gelatin capsules and methods for converting gelatin capsules into controlled release dosage forms.

BACKGROUND OF THE INVENTION

Osmotic dosage systems comprising means for delivering a solid drug formulation by displacing physically the solid drug formulation from the osmotic system are known to the prior art in U.S. Pat. Nos. 4,327,725; 4,612,008; 4,765,989; and 4,783,337.

An osmotic system comprising means for displacing physically a liquid drug formulation from an osmotic system is known to the prior art in U.S. Pat. No. 4,627,850. U.S. Pat. No. 3,995,631 describes a dosage form having an impermeable flexible bag containing a liquid drug formulation surrounded by an osmotic layer. U.S. Pat. No. 4,203,440 describes a somewhat similar configuration in which a semipermeable layer in which is dispersed an ion exchange resin forms an osmotic layer surrounding a flexible bag from which drug is dispensed. U.S. Pat. No. 4,627,850 describes a capsule surrounded by an osmotic layer and outer, semipermeable layer to dispense drug from the capsule upon expansion of the osmotic layer. U.S. Pat. No. 5,324,280, which is incorporated herein by reference, describes a gelatin capsule filled with a liquid drug formulation wherein the capsule is surrounded by an osmotic layer and an outer, semipermeable layer. Upon imbibing fluid that passes through the semipermeable membrane, the osmotic layer expands and forces the liquid drug formulation from an exit passageway formed in the end of the dosage form. While the foregoing system of U.S. Pat. No. 5,324,280 may provide controlled release of the active agent in particular circumstances, its use with gelatin capsules has not been entirely satisfactory for wide application.

SUMMARY OF THE INVENTION

In one aspect, the invention comprises a dosage form comprising (a) a gelatin capsule containing a liquid, active agent formulation; (b) a multilayer wall superposed on the gelatin capsule comprising, in outward order from the capsule: (i) a barrier layer, (ii) an expandable layer, and (iii) a semipermeable layer; and (c) an orifice formed or formable through the wall.

In another aspect, the invention comprises a dosage form comprising a gelatin capsule containing a liquid, active agent formulation, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall.

In yet another aspect, the invention comprises a method of converting a gelatin capsule containing a liquid, active agent formulation into a controlled release dosage form which comprises forming a composite wall on the gelatin capsule by sequentially forming a barrier layer on the external surface of the gelatin capsule, an expandable layer on the barrier layer and a semipermeable layer on the expandable layer. An exit orifice may be formed in the wall directly, as by drilling, e.g., such as with a laser, or the exit orifice may be formed by sequentially forming an opening in the composite wall having a diametric dimension greater than the desired final diameter of the exit orifice, plugging the hole with a material in which the exit orifice may be formed, and then forming an exit orifice in the plug.

In still another aspect, the invention comprises a method of manufacturing a controlled release dosage form comprising a gelatin capsule containing a liquid, active agent formulation, which method comprises the steps of (1) forming a barrier layer surrounding the gelatin capsule containing a liquid, active agent formulation; (2) forming an expandable layer surrounding the barrier layer-gelatin capsule; (3) removing a portion of the expandable layer in an area in which an exit orifice is to be located without compromising the integrity of the barrier layer in the area; (4) forming a semipermeable layer surrounding the intermediate dosage form prepared through step (4); and forming an exit orifice in the area exposing at least a portion of the gelatin capsule. One or more of the layers may be formed by coating.

In yet another aspect, the invention comprises a dosage form comprising a gelatin capsule containing a liquid, active agent formulation, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice.

In another aspect, the invention comprises a dosage form comprising a gelatin capsule containing a liquid, active agent formulation, the gelatin capsule being surrounded by a barrier layer contacting the external surface of the gelatin capsule, an expandable layer contacting a portion of the barrier layer, a semipermeable layer encompassing at least the expandable layer, and an exit orifice formed or formable in the dosage form extending from the external surface of the gelatin capsule to the environment of use. The expandable layer may be formed in one or more discrete sections, such as for example, two sections located on opposing sides or ends of the gelatin capsule.

BRIEF DESCRIPTION OF THE DRAWINGS

The drawing figures, which are not drawn to scale, are set forth to illustrate various embodiments of the invention.

In the drawing figures and in the specification, like parts in related figures are identified by like numerals. The terms appearing earlier in the specification and in description of the drawing figures, as well as embodiments thereof, are further detailed below.

DETAILED DESCRIPTION OF THE INVENTION

The present invention is a significant improvement over the systems described in U.S. Pat. No. 5,324,580, the disclosure of which is incorporated herein by reference. Systems prepared in accordance with the teaching of that patent were unable to provide a dosage form from which precise delivery of the active agent would occur in all cases. It appears that in the prior art system the interaction of fluid from the environment of use, agents forming the osmotic layer, materials forming the gelatin layer and components of the liquid, active agent formulation presented a complex system that could not reproducibly provide the precisely-controlled release of the active agent required for many applications. Surprisingly, it has been discovered that the imposition of a barrier layer, which will be described in detail hereinafter, between a gelatin capsule containing a liquid, active agent formulation and the expandable layer permits the simple and economical construction of useful controlled release dosage forms from conventionally manufactured gelatin capsules. Dosage forms of this invention permit delivery of the active agent in a controlled fashion from the completely fabricated dosage form.

Figure 1:
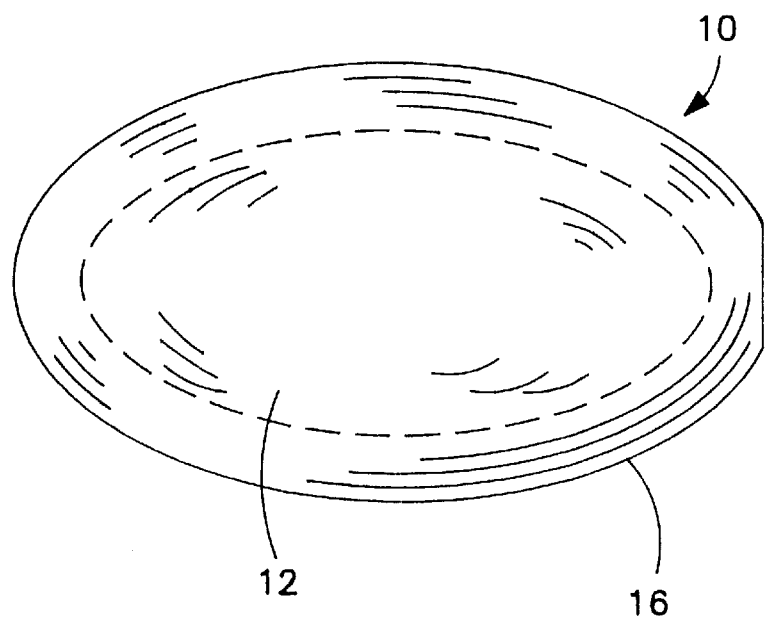
FIG. 1 is an overall view of a dosage form of one embodiment of the invention for delivering an active agent to an environment of use.
Figure 2:
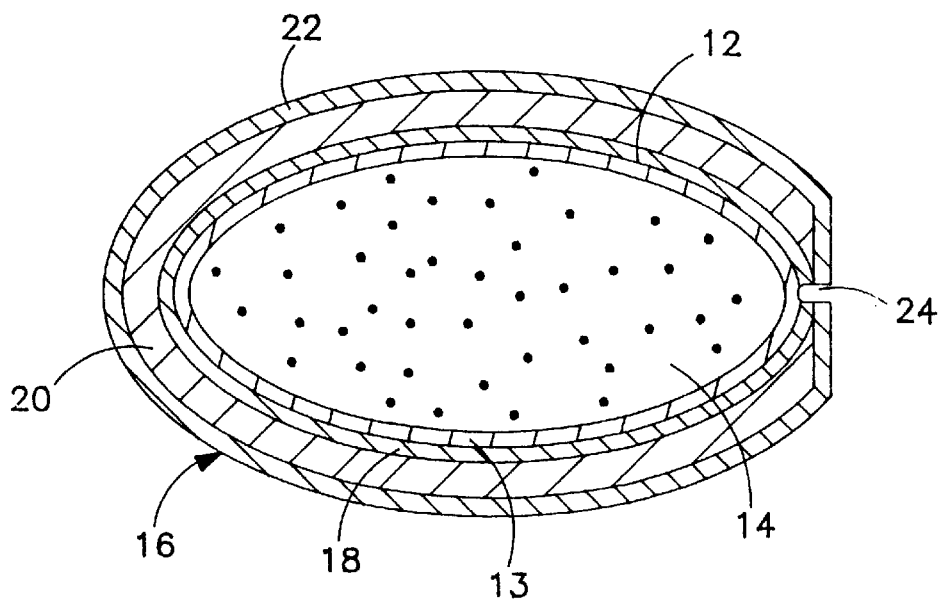
FIG. 2 is an opened view of the dosage form of FIG. 1 illustrating the structure of the system comprising a sealed, gelatin capsule enclosing a useful active agent formulation.

Turning now to the drawing figures in detail, which drawing figures are not to be construed as limiting, one embodiment of a dosage form of the invention is illustrated in FIG. 1. In FIG. 1, a dosage form 10 comprises a gelatin capsule 12 and a composite wall 16 that surrounds the capsule 12. As can be seen more clearly by reference to FIG. 2, gelatin capsule 12 is surrounded by a barrier layer 18, except in the area in which the exit orifice 24 is formed. Barrier layer 18 is itself surrounded by an expandable layer 20, which is itself surrounded by an external semipermeable layer 22. An exit orifice 24 is formed through external layer 22, expandable layer 20 and barrier layer 18, but does not extend through the wall of gelatin capsule 12 (although it may extend part of the way into the capsule wall). The exit orifice 24 may be formed as an opening as shown; or, while not shown, exit orifice 24 could be formed of a solid or semi-solid material that will dissolve, leach out, or otherwise provide an opening extending from the environment of use to the wall of the gelatin capsule to permit release of the liquid, active agent formulation when the dosage form is in the environment of use.

External layer 22 comprises a semipermeable composition permeable to the passage of fluid in the environment of use and essentially impermeable to the passage of drugs and materials forming the expandable layer, which in one embodiment may contain osmotic agents. Expandable layer 20 comprises in one embodiment a hydroactivated composition that swells in the presence of water, such as that present in gastric fluids. Conveniently, it may comprise an osmotic composition comprising an osmotic solute that exhibits an osmotic pressure gradient across semipermeable layer 22 against an external fluid present in the environment of use. In another embodiment, hydro-activated layer 20 comprises a hydrogel that imbibes and/or absorbs fluid into layer 20 through outer semipermeable layer 22. Semipermeable layer 22 is non-toxic. It maintains its physical and chemical integrity during operation and it is essentially free of interaction with expandable layer 20. Gelatin capsule 12 may be a conventional gelatin capsule, and may be formed in two sections or as a single unit capsule in its final manufacture. Preferably, due to the presence of the barrier layer, the wall of capsule 12 will retain its integrity and gel-like characteristics, except where it dissolves in the area exposed to the exit orifice, thereby resulting in well-controlled delivery of the active agent formulation. However, some dissolution of the gelatin capsule extending from the exit orifice during delivery of the active agent may be accommodated without significant impact on the delivery of active agent.

The gelatin capsule will contain an effective amount of a therapeutic agent in a liquid, active-agent formulation 14. The liquid, active agent formulation may be in any form that can be dispensed from the inside of the gelatin capsule through the exit orifice. The formulation, for example, may be neat, liquid active agent, liquid active agent in a solution, suspension, emulsion or self-emulsifying composition, or the like, or a liposomal solution of active agent or a solid formulation of active agent that liquifies at the temperature of the environment of use, or a solid active agent in solution, suspension or slurry. Optionally other dosage-forming ingredients, such as an anti-oxidant, a suspending agent, a surface active agent, and the like may be present in the liquid, active agent formulation. The liquid, active agent formulation will be released through at least one exit orifice 24 to an environment of use.

The gelatin capsule may be manufactured in accordance with conventional methods as a single body unit comprising the standard capsule shape. The single-body soft gelatin capsule typically may be provided in sizes from 3 to 22 minims (1 minimim being equal to 0.0616 ml) and in shapes of oval, oblong or others. The gelatin capsule may also be manufactured in accordance with conventional methods as a two-piece hard gelatin capsule, typically in standard shape and various standard sizes, conventionally designated as (000), (00), (0), (1), (2), (3), (4), and (5). The largest number corresponds to the smallest size. Non-standard shapes may be used as well. In either case of soft, gelatin capsule or hard gelatin capsule, non-conventional shapes and sizes may be provided if required for a particular application. The gelatin capsule should have a deformable wall and typically will be a soft capsule; although a hard capsule that becomes soft during operation, such as by hydration, may be used as well. The soft capsule is made by various processes including the plate process, the rotary die process, the reciprocating die process, and the continuous process. The plate process uses a set of molds. A warm sheet of a prepared capsule-wall forming material is laid over a lower mold and the agent formulation poured on it. A second sheet of wall-forming material is placed over the agent formulation followed by the top mold. The mold is placed under a press and a pressure applied, with or without heat to form a unit, soft capsule member. The capsules are washed with a solvent for removing excess agent formulation from the exterior of the capsule The rotary die process for providing a capsule comprises two continuous films of capsule wall-forming materials that are brought into convergence between a pan of revolving dies and an injector wedge. The process fills and seals the capsule in dual and coincident operations. In this process, the sheets of capsule wall-forming compositions are fed over guide rolls, and then down between the wedge injector and the die rolls. The agent formulation to be capsulated flows by gravity into a positive displacement pump. The pump meters the agent formulation through the wedge injector and into the sheets between the die rolls. The bottom of the wedge contains small orifices lined-up with the die pickets of the die rolls. The capsule is about half-sealed when the pressure of pumped active agent formulation forces the sheets into the die pockets. The soft capsules are simultaneously filled, shaped, hermetically sealed and cut from the sheets of wall-forming compositions. The sealing of the soft capsule is achieved by mechanical pressure on the die rolls and by heating the sheets of wall-forming composition by the wedge. After the manufacture, the liquid, active agent formulation-filled capsules are dried in the presence of forced air, and a barrier layer, an expandable layer and a semipermeable wall formed thereon, by processes described hereafter.

The reciprocating die process produces soft capsules by leading two films of capsule wall-forming compositions between a set of vertical dies. The dies, as they close, open, and close, perform as a continuous vertical plate forming row after row of pockets across the film. The pockets are filled with liquid, active agent formulation, and, as the pockets move through the dies, they are sealed, shaped and cut from the moving film as capsules filled with agent formulation. The continuous process is a manufacturing system that also uses rotary dies.

Alternatively, the gelatin capsule may be made conveniently in two parts, with one part (the "cap") slipping over and capping the other part (the "body") as long as the gelatin capsule is deformable under the forces exerted by the expandable layer 20 and seals to prevent leakage of the liquid, active agent formulation from between the telescoping portions of the body and cap. The two parts completely surround and capsulate the internal lumen that contains the liquid, active agent formulation, which may contain, as described above, useful additives. The two parts are fitted together after the body is filled with a preselected formulation. The assembly is done by slipping or telescoping the cap section over the body section, and sealing the cap and body, thereby completely surrounding and encapsulating the formulation of active agent.

Soft gelatin capsules typically have a wall thickness that is greater than the wall thickness of hard gelatin capsules. For example, soft gelatin capsules may have a wall thickness on the order of 10–40 mils, about 20 mils being typical, whereas hard gelatin capsules may have a wall thickness on the order of 2–6 mils, about 4 mils being typical.

In one embodiment of the dosage system, gelatin capsule 12 may be of single unit construction and may be surrounded by an unsymmetrical hydro-activated layer as the expandable layer. The unsymmetrical, expandable layer 20 will have a thicker portion remote from the exit orifice 24. As hydro-activated layer 20 imbibes and/or absorbs external fluid, it expands and applies a push pressure against the wall of gelatin capsule 12 and barrier layer 18 and forces active agent formulation through the exit orifice 24. The presence of the unsymmetrical layer functions to assure that the maximum dose of agent is delivered from the dosage form, as the thicker section of layer 20 distant from passageway 24 swells and moves towards passageway 21.

Figure 14A:
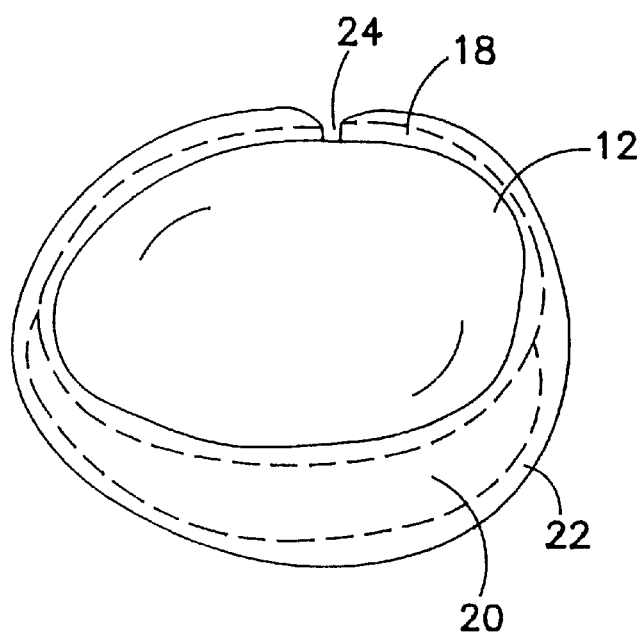
FIGS. 14A and 14B illustrate an alternate embodiment of a dosage form of the invention wherein the expandable layer is formed on one side of the gelatin capsule.
Figure 14B:
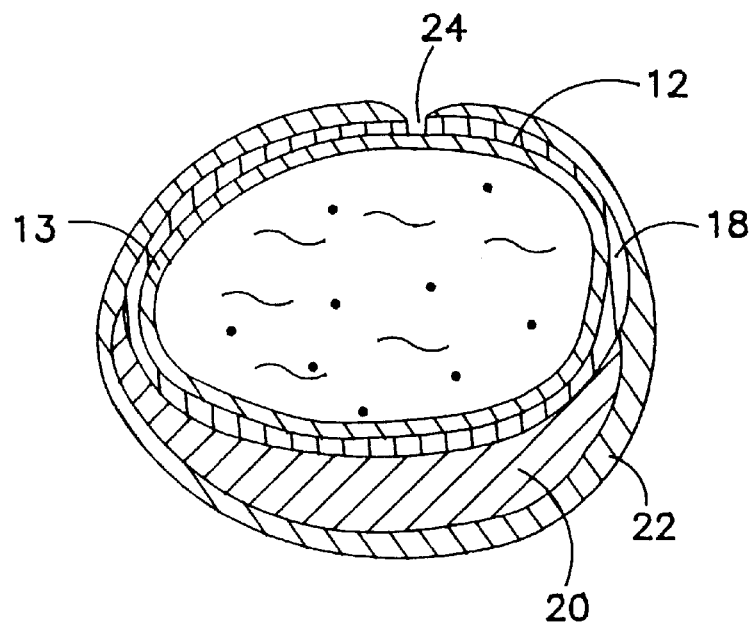

In yet another configuration, the expandable layer 20 may be formed in discrete sections that do not entirely encompass the barrier layer-coated gelatin capsule. As can be seen from FIGS. 14A and 14B, expandable layer 20 may be a single element that is formed to fit the shape of the gelatin capsule at the area of contact. FIG. 14A is a schematic of the completed dosage form 10 with the various components of the dosage form indicated by dashed lines and the gelatin capsule indicated by a solid line. FIG. 14B is a cross-sectional view of a completed dosage form 10 having one, discrete expandable section that does not completely encompass the gelatin capsule. Expandable layer 20 may be fabricated conveniently by tableting to form the concave surface that is complementary to the external surface of the barrier-coated gelatin capsule. Appropriate tooling such as a convex punch in a conventional tableting press can provide the necessary complementary shape for the expandable layer 20. In this case, expandable layer 20 is granulated and compressed, rather than formed as a coating. The methods of formation of an expandable layer 20 by tableting are well known, having been described, for example in U.S. Pat. Nos. 4,915,949; 5,126,142; 5,660,861; 5,633,011; 5,190,765; 5,252,338; 5,620,705; 4,931,285; 5,006,346; 5,024,842; and 5,160,743, which are incorporated herein by reference.

In the embodiment shown in FIGS. 14A and 14B, the barrier layer 18 is first coated onto the gelatin capsule 12 and then the tableted, expandable layer 20 is attached to the barrier-coated gelatin capsule with a biologically compatible adhesive. Suitable adhesives include, for example, starch paste, aqueous gelatin solution, aqueous gelatin/glycerin solution, acrylate-vinylacetate based adhesives such as Duro-Tak adhesives (National Starch and Chemical Company), aqueous solutions of water soluble hydrophilic polymers such as hydroxypropyl methyl cellulose, hydroxymethyl cellulose, hydroxyethyl cellulose, and the like. That intermediate dosage form is then coated with a semipermeable layer. The exit orifice 24 is formed in the side or end of the gelatin capsule 12 opposite the expandable layer section 20. As the expandable layer 20 imbibes fluid, it will swell. Since it is constrained by the semipermeable layer 22, as it expands it will compress the barrier-coated gelatin capsule and express the liquid, active agent formulation from the interior of the gelatin capsule into the environment of use.

Figure 16A:
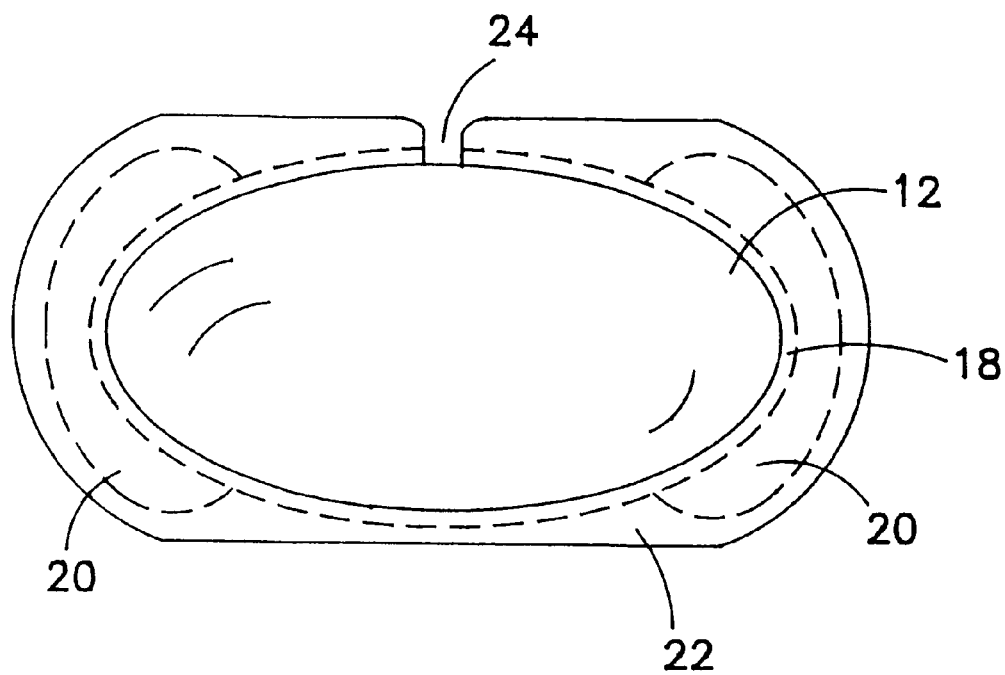
FIGS. 16A and 16B illustrate still another embodiment of a dosage form of the invention wherein the expandable layer is formed on opposed ends of the gelatin capsule.
Figure 16B:
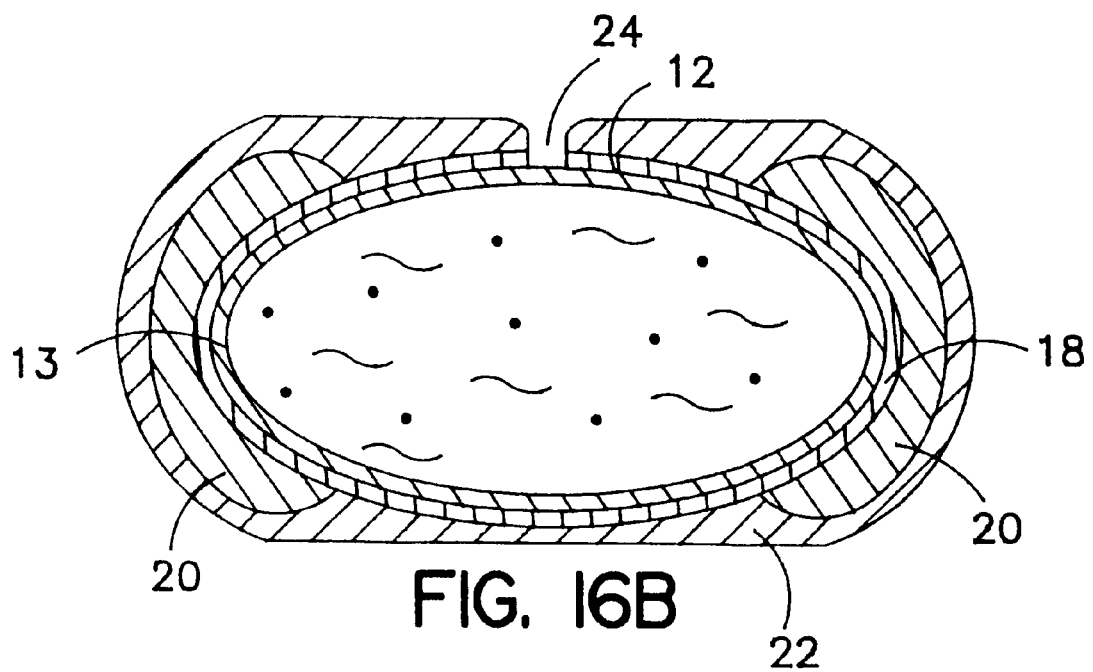

In yet another configuration, expandable layer 20 is formed as a plurality of discrete sections. The number of discrete sections may be from 2–6, but often the use of two sections is adequate to obtain a desired release profile. For example, two sections may be fitted over the ends of the barrier-coated gelatin capsule as illustrated in FIGS. 16A and 16B. FIG. 16A is a schematic of the completed dosage form 10 with the various components of the dosage form indicated by dashed lines and the gelatin capsule indicated by a solid line. FIG. 16B is a cross-sectional view of a completed dosage form 10 having two, discrete expandable sections 20. Each expandable section 20 is conveniently formed by tableting from granules and is adhesively attached to the barrier-coated gelatin capsule, preferably on the ends of the capsule 12. Then a semipermeable layer 22 is coated on the intermediate dosage form and an exit orifice 24 is formed in a side of the dosage form between the expandable sections. As sections 20 expand upon imbibing fluid from the environment of use, the liquid, active agent formulation will be expressed from the interior of capsule 12 in a controlled manner to provide controlled-release delivery of the liquid active agent formulation from the interior of gelatin capsule 12.

The dosage forms prepared in accordance with this invention are suitable for delivery of a liquid, active agent formulation to the environment of use over a prolonged period of time. For purposes hereof, a "prolonged period of time" may be several hours or more. Typically for human and veterinary pharmaceutical applications, the prolonged period of time may be from 2 hours to 24 hours, more often 4 hours to 12 hours or 6–8 hours, since dosing typically takes place several times a day. For many applications it may be preferable to provide dosage forms that only need to be administered once-a-day.

While drawing FIGS. 1 through 10, FIGS. 14A and 14B and FIGS. 16A and 16B are illustrative of various systems primarily directed to oral pharmaceutical and veterinary applications that can be provided according to the invention, it is to be understood these devices are not to be construed as limiting, as these systems can take a wide variety of shapes, sizes and forms adapted for delivering a active agent to the environment of use. For example, the dosage forms comprise buccal, implant, anal, artificial gland, cervical, intrauterine, ear, nose, dermal, vaginal, percutaneous, subcutaneous and like delivery systems. The pharmaceutical applications of the dosage system embraces ethical and proprietary products for human and veterinary use. The osmotic system can be used also for packaging and delivering breath fresheners, perfumes, bath oils containing dermal medicaments, bubble baths containing therapeutics and the like. The osmotic system also can be sized, shaped, structured and adapted for delivering an active agent in streams, aquariums, fields, factories, reservoirs, laboratory facilities, hot houses, transportation means, military means, hospitals, veterinary clinics, nursing homes, farms, zoos, sickrooms, clinics, and other places of use.

In accordance with the practice of this invention, dosage form 10 may be provided with a semipermeable layer 22 comprising a composition that does not adversely affect the host, the active agent, or any osmopolymer, or osmagent, and the like that may be present in the expandable layer 20 of the dosage form. The semipermeable wall is permeable to the passage of fluid such as water and biological fluids, and it is substantially impermeable to the passage of active agent, and materials forming the expandable layer, which may contain an osmagent, an osmopolymer, and the like. For ease of manufacture, it is preferred that the whole of external layer 22 be semipermeable. In those circumstances where only a portion of external layer 22 is semipermeable, there should be fluid communication between the semipermeable portion and expandable layer 20 to permit layer 20 to imbibe fluid and expand during dispensing of the active agent formulation. The semipermeable compositions used for forming layer 22 are essentially non-erodible, and they are insoluble in biological fluids during the operational lifetime of the osmotic system.

Representative polymers for forming layer 22 comprise semipermeable homopolymers, semipermeable copolymers, and the like. In one presently preferred embodiment, the compositions comprise cellulose esters, cellulose ethers, and cellulose ester-ethers. The cellulosic polymers have a degree of substitution, "D.S.", on their anhydroglucose unit that are replaced by a substituting group, or converted into another group. The anhydroglucose unit can be partially or completely substituted with groups such as acyl, alkanoyl, alkenoyl, aroyl, alkyl, alkoxy, carboalkyl, alkylcarbamate, alkylcarbonate, alkylsulfonate, and alkylsulfamate, typically having 1–12 carbon atoms, halogen, semipermeable polymer forming groups, and the like.

The semipermeable compositions typically include a member selected from the group consisting of cellulose acylate, cellulose diacylate, cellulose triacylate, cellulose triacetate, cellulose acetate, cellulose diacetate, cellulose triacetate, mono-, di- and tri-cellulose alkanylates, mono-, di-, and tri-alkenylates, mono-, di- and tri-aroylates, and the like. Exemplary polymers include cellulose acetate-have a D.S. of 1.8 to 2.3 and an acetyl content of 32 to 39.9%; cellulose diacetate having a D.S. of 1 to 2 and an acetyl content of 21 to 35%, cellulose triacetate having a D.S. of 2 to 3 and an acetyl content of 34 to 44.8% and the like. More specific cellulosic polymers include cellulose propionate having a D.S. of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45%, and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29%, a butyryl content of 17 to 53%, and a hydroxyl content of 0.5 to 4.7%; cellulose triacylates having a D.S. of 2.6 to 3 such as cellulose trivalerate, cellulose trilamate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate, and the like; mixed cellulose esters such as cellulose acetate valerate, cellulose acetate succinate, cellulose propionate succinate, cellulose acetate octanoate, cellulose valerate palmitate, cellulose acetate heptanoate, and the like.

Semipermeable polymers are known in U.S. Pat. No. 4,077,407 and they can be synthesized by procedures described in *Encyclopedia of Polymer Science and Technology*, Vol. 3, pages 325 to 354, 1964, published by Interscience Publishers, Inc., New York.

Additional semipermeable polymers for forming layer 22 comprise cellulose acetaldehyde dimethyl acetate; cellulose acetate ethylcarbamate; cellulose acetate methylcarbamate; cellulose dimethylaminoacetate; semipermeable polyamide; semipermeable polyurethanes; semipermeable sulfonated polystyrenes; cross-linked selectively semipermeable polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb et at. in U.S. Pat. No. 3,133,132; semipermeable polystyrene derivatives; semipermeable poly (sodium styrenesulfonate); semipermeable poly (vinylbenzyltremethyl-ammonium chloride); semipermeable polymers, exhibiting a fluid permeability of $10^{-5}$ to $10^{-2}$ (cc.mil/cm hr.atm) expressed as per atmosphere of hydrostatic or osmotic pressure differences across a semipermeable wall. The polymers are known to the art in U.S. Pat. Nos. 3,845,770; 3,916,899; and 4,160,020; and in *Handbook of Common Polymers*, by Scott, J. R. and Roff, W. J., 1971, published by CRC Press, Cleveland, Ohio.

Semipermeable layer 22 also can comprise a flux regulating agent. The flux regulating agent is a compound added to assist in regulating the fluid permeability or flux through layer 22. The flux regulating agent can be a flux enhancing agent or a decreasing agent. The agent can be preselected to increase or decrease the liquid flux. Agents that produce a marked increase in permeability to fluids such as water are often essentially hydrophilic, while those that produce a marked decrease to fluids such as water are essentially hydrophobic. The amount of regulator in the wall when incorporated therein generally is from about 0.01% to 20% by weight or more. The flux regulator agents in one embodiment that increase flux include polyhydric alcohols, polyalkylene glycols, polyalkylenediols, polyesters of alkylene glycols, and the like. Typical flux enhancers include polyethylene glycol 300, 400, 600, 1500, 4000, 6000, poly (ethylene glycol-co-propylene glycol), and the like; low molecular weight gylcols such as polypropylene glycol, polybutylene glycol and polyamylene glycol: the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; esters such as ethylene glycol dipropionate, ethylene glycol butyrate, butylene glucol dipropionate, glycerol acetate esters, and the like. Representative flux decreasing agents include phthalates substituted with an alkyl or alkoxy or with both an alkyl and alkoxy group such as diethyl phthalate, dimethoxyethyl phthalate, dimethyl phthalate, and [di(2-ethylhexyl) phthalate], aryl phthalates such as triphenyl phthalate, and butyl benzyl phthalate; insoluble salts such as calcium sulphate, barium sulphate, calcium phosphate, and the like; insoluble oxides such as titanium oxide; polymers in powder, granule and like form such as polystyrene, polymethylmethacrylate, polycarbonate, and polysulfone; esters such as citric acid esters esterfied with long chain alkyl groups; inert and substantially water impermeable fillers; resins compatible with cellulose based wall forming materials, and the like.

Other materials that can be used to form the layer 22 for imparting flexibility and elongation properties to the layer, for making layer 22 less-to-nonbrittle and to render tear strength, include phthalate plasticizers such as dibenzyl phthalate, dihexyl phthalate, butyl octyl phthalate, straight chain phthalates of six to eleven carbons, di-isonony phthalte, di-isodecyl phthalate, and the like. The plasticizers include nonphthalates such as triacetin, dioctyl azelate, epoxidized tallate, tri-isoctyl trimellitate, tri-isononyl trimellitate, sucrose acetate isobutyrate, epoxidized soybean oil, and the like. The amount of plasticizer in a wall when incorporated therein is about 0.01% to 20% weight, or higher.

The expandable layer 20 in one preferred embodiment comprises a hydroactive layer comprising a hydrophilic polymer, also known as osmopolymers. The osmopolymers exhibit fluid imbibition properties. The osmopolymers are swellable, hydrophilic polymers, which osmopolymers interact with water and biological aqueous fluids and swell or expand to an equilibrium state. The osmopolymers exhibit the ability to swell in water and biological fluids and retain a significant portion of the imbibed fluid within the polymer structure. The osmopolymers swell or expand to a very high degree, usually exhibiting a 2 to 50 fold volume increase. The osmopolymers can be noncross-linked or cross-linked. The swellable, hydrophilic polymers are in one embodiment lightly cross-linked, such cross-links being formed by covalent or ionic bonds or residue crystalline regions after swelling. The osmopolymers can be of plant, animal or synthetic origin.

The osmopolymers are hydrophilic polymers. Hydrophilic polymers suitable for the present purpose include poly (hydroxy-alkyl methacrylate) having a molecular weight of from 30,000 to 5,000,000; poly (vinylpyrrolidone) having a molecular weight of from 10,000 to 360,000; anionic and cationic hydrogels; polyelectrolytes complexes; poly (vinyl alcohol) having a low acetate residual, cross-linked with glyoxal, formaldehyde, or glutaraldehyde and having a degree of polymerization of from 200 to 30,000; a mixture of methyl cellulose, cross-linked agar and carboxymethyl cellulose; a mixture of hydroxypropyl methylcellulose and sodium carboxymethylcellulose; a mixture of hydroxypropyl ethylcellulose and sodium carboxymethyl cellulose, a mixture of sodium carboxymethylcellulose and methylcellulose, sodium carboxymethylcellulose; potassium carboxymethylcellulose; a water insoluble, water swellable copolymer formed from a dispersion of finely divided copolymer of maleic anhydride with styrene, ethylene, propylene, butylene or isobutylene crosslinked with from 0.001 to about 0.5 moles of saturated cross-linking agent per mole of maleic anhydride per copolymer; water swellable polymers of N-vinyl lactams; polyoxyethylene-polyoxypropylene gel; carob gum; polyacrylic gel; polyester gel; polyuria gel; polyether gel, polyamide gel; polycellulosic gel; polygum gel; initially dry hydrogels that imbibe and absorb water which penetrates the glassy hydrogel and lowers its glass temperature; and the like.

Representative of other osmopolymers comprise polymers that form hydrogels such as Carbopol® acidic carboxypolymer, a polymer of acrylic acid cross-linked with a polyallyl sucrose, also known as carboxypolymethylene, and carboxyvinyl polymer having a molecular weight of 250,000 to 4,000,000; Cyanamer® polyacrylamides; cross-linked water swellable indenemaleic anhydride polymers; Good-rite® polyacrylic acid having a molecular weight of 80,000 to 200,000; Polyox® polyethylene oxide polymer having a molecular weight of 100,000 to 5,000,000 and higher; starch graft copolymers; Aqua-Keeps® acrylate polymer polysaccharides composed of condensed glucose units such as diester cross-linked polygluran; and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels; and in *Handbook of Common Polymers*, by Scott and Roff, published by the Chemical Rubber Co., Cleveland, Ohio. The amount of osmopolymer comprising a hydro-activated layer may be from 5% to 100%.

The expandable layer 20 in another manufacture comprises an osmotically effective compound that comprises inorganic and organic compounds that exhibit an osmotic pressure gradient across a semipermeable wall against an external fluid. The osmotically effective compounds, as with the osmopolymers, imbibe fluid into the osmotic system, thereby making available fluid to push against barrier layer 18 and the wall of gelatin capsule 12 for pushing active agent from the dosage form. The osmotically effective compounds are known also as osmotically effective solutes, and also as osmagents. Osmotically effective solutes that may be used comprise magnesium sulfate, magnesium chloride, potassium sulfate, sodium sulfate, lithium sulfate, potassium acid phosphate, mannitol, urea, inositol, magnesium succinate, tartaric acid, carbohydrates such as raffinose, sucrose, glucose, lactose, sorbitol, and mixtures therefor. The amount of osmagent in layer 20 may be from 5% to 100% of the weight of the layer. Layer 20 optionally comprises an osmopolymer and an osmagent with the total amount of osmopolymer and osmagent equal to 100%. Osmotically effective solutes are known to the prior art as described in U.S. Pat. No. 4,783,337.

The barrier layer 18 will be deformable under the pressure exerted by the expandable layer 20 and will be impermeable (or less permeable) to fluids and materials that may be present in the expandable layer, the liquid active agent formulation within the gelatin capsule and in the environment of use, during delivery of the active agent formulation. A certain degree of permeability of the barrier layer may be permitted if the delivery rate of the active agent formulation is not detrimentally effected. However, it is preferred that barrier layer 18 not completely transport through it fluids and materials in the dosage form and the environment of use during the period of delivery of the active agent. Barrier layer 18 will be deformable under forces applied by expandable layer 20 so as to permit compression of capsule 12 to force the liquid, active agent formulation from the exit orifice. Preferably, barrier layer 18 will be deformable to such an extent that it create a seal between the expandable layer 22 and the semipermeable layer 22 in the area where the exit orifice is formed. In that manner, barrier layer 18 will deform or flow to a limited extent to seal the initially, exposed areas of the expandable layer 20 and the semipermeable layer 22 when the exit orifice is being formed, such as by drilling or the like, or during the initial stages of operation. When sealed, the only avenue for liquid permeation into the expandable layer is through the semipermeable layer, and there is no back-flow of fluid into the expandable layer through the exit orifice.

Suitable materials for forming the barrier layer may include, for example, polyethylene, polystyrene, ethylene-vinyl acetate copolymers, polycaprolactone and Hytrel® polyester elastomers (Du Pont), cellulose acetate, cellulose acetate pseudolatex (such as described in U.S. Pat. No. 5,024,842), cellulose acetate propionate, cellulose acetate butyrate, ethyl cellulose, ethyl cellulose pseudolatex (such as Surelease® as supplied by 10 Colorcon, West Point, Pa. or Aquacoat™ as supplied by FMC Corporation, Philadelphia, Pa.), nitrocellulose, polylactic acid, poly- glycolic acid, polylactide glycolide copolymers, collagen, polyvinyl alcohol, polyvinyl acetate, polyethylene vinylacetate, polyethylene teraphthalate, polybutadiene styrene, polyisobutylene, polyisobutylene isoprene copolymer, polyvinyl chloride, polyvinylidene chloride-vinyl chloride copolymer, copolymers of acrylic acid and methacrylic acid esters, copolymers of methylmethacrylate and ethylacrylate, latex of acrylate esters (such as Eudragit® supplied by RöhmPharma, Darmstaat, Germany), polypropylene, copolymers of propylene oxide and ethylene oxide, propylene oxide ethylene oxide block copolymers, ethylenevinyl alcohol copolymer, polysulfone, ethylene vinylalcohol copolymer, polyxylylenes, polyalkoxysilanes, polydimethyl siloxane, polyethylene glycol-silicone elastomers, electromagnetic irradiation crosslinked acrylics, silicones, or polyesters, thermally crosslinked acrylics, silicones, or polyesters, butadiene-styrene rubber, and blends of the above.

Preferred materials include cellulose acetate, copolymers of acrylic acid and methacrylic acid esters, copolymers of methylmethacrylate and ethylacrylate, and latex of acrylate esters. Preferred copolymers include poly (butyl methacrylate), (2-dimethylaminoethyl)methacrylate, methyl methacrylate) 1:2:1, 150,000, sold under the trademark EUDRAGIT E; poly (ethyl acrylate, methyl methacrylate) 2:1, 800,000, sold under the trademark EUDRAGIT NE 30 D; poly (methacrylic acid, methyl methacrylate) 1:1, 135,000, sold under the trademark EUDRAGIT L; poly (methacrylic acid, ethyl acrylate) 1:1, 250,000, sold under the trademark EUDRAGIT L; poly (methacrylic acid, methyl methacrylate) 1:2, 135,000, sold under the trademark EUDRAGIT S; poly (ethyl acrylate, methyl methacrylate, trimethylammonioethyl methacrylate chloride) 1:2:0.2, 150,000, sold under the trademark EUDRAGIT RL; poly (ethyl acrylate, methyl methacrylate, trimethylammonioethyl methacrylate chloride) 1:2:0.1, 150,000, sold as EUDRAGIT RS. In each case, the ratio x:y:z indicates the molar proportions of the monomer units and the last number is the number average molecular weight of the polymer. Especially preferred are cellulose acetate containing plasticizers such as acetyl tributyl citrate and ethylacrylate methylmethacrylate copolymers such as Eudragit NE.

The foregoing materials for use as the barrier layer may be formulated with plasticizers to make the barrier layer suitably deformable such that the force exerted by the expandable layer 20 will collapse the compartment formed by the barrier layer 18 and gelatin capsule 12 to dispense the liquid, active agent formulation. Examples of typical plasticizers are as follows: polyhydric alcohols, triacetin, polyethylene glycol, glycerol, propylene glycol, acetate esters, glycerol triacetate, triethyl citrate, acetyl triethyl citrate, glycerides, acetylated monoglycerides, oils, mineral oil, castor oil and the like. The plasticizers may be blended into the material in amounts of 10–50 weight percent based on the weight of the material.

The various layers forming the barrier layer, expandable layer (when not a tabletted composition) and semipermeable layer may be applied by conventional coating methods such as described in U.S. Pat. No. 5,324,280, previously incorporated herein by reference. While the barrier layer, expandable layer and semipermeable layer forming the multilayer wall superposed on the gelatin capsule have been illustrated and described for convenience as single layers, each of those layers may be composites of several layers. For example, for particular applications it may be desirable to coat the gelatin capsule with a first layer of material that facilitates coating of a second layer having the permeability characteristics of the barrier layer. In that instance, the first and second layers comprise the barrier layer as used herein. Similar considerations would apply to the semipermeable layer and the expandable layer.

Gelatin capsule 12 may be conventional, and typically comprises capsule forming compositions comprising gelatin, gelatin having a viscosity of 15 to 30 millipoises and a bloom strength up to 150 grams; gelatin having a bloom value of 160 to 250; a composition comprising gelatin, glycerine, water and titanium dioxide; a composition comprising gelatin, erythrosin, iron oxide and titanium dioxide; a composition comprising gelatin, glycerine, sorbitol, potassium sorbate and titanium dioxide; a composition comprising gelatin, acacia glycerine, and water; and the like. Materials useful for forming capsule walls are known in U.S. Pat. Nos. 4,627,850; and in 4,663,148.

A plasticizer may be compounded with the wall of the gelatin capsule 12 and the barrier layer 18 for increasing the flow prospects and for enhancing the workability of the polymer during manufacture of the capsule or the barrier layer. For example, glycerin can be used for plasticizing gelatin, pectin, casein or polyvinyl alcohol. Other plasticizers that can be used for the present purpose compare triethyl citrate, diethyl phthalate, diethyl sebacate and the like. The amount of plasticizer when present is from 0.05 to 30% of the weight of the composition.

The expression "orifice" or "exit orifice" as used herein comprises means suitable for releasing the active agent from the dosage form. The expression includes aperture, orifice, hole, bore, pore, porous element, porous overlay, porous insert, hollow fiber, capillary tube, microporous insert, microporous overlay, and the like. In a preferred embodiment, the exit orifice 24 will extend only through the external layer 22, the expandable layer 20 and the barrier layer 18 to the external wall of gelatin capsule 12. However, the exit orifice 24 may extend partially into the wall of gelatin capsule 12 as long as it does not completely traverse the wall. When exposed to the environment of use, the fluids in the environment of use may dissolve the wall of gelatin capsule 12 where exposed by the exit orifice 24; or the pressure exerted on the gelatin capsule 12 and the barrier layer 18 by the expandable layer 20 may cause the gelatin capsule wall to rupture where exposed to the exit orifice 24. In either case, the interior of gelatin capsule 12 will be placed in fluid communication with the environment of use, and the liquid, active agent formulation will be dispensed through exit orifice 24 as the barrier layer 18 and the gelatin capsule 12 are compressed.

The exit orifice can be formed by mechanical drilling, laser drilling, eroding an erodible element, extracting, dissolving, bursting, or leaching a passageway former from the composite wall. The passageway can be a pore formed by leaching sorbitol, lactose or the like from a wall or layer as disclosed in U.S. Pat. No. 4,200,098. This patent discloses pores of controlled-size porosity formed by dissolving, extracting, or leaching a material from a wall, such as sorbitol from cellulose acetate. A preferred form of laser drilling is the use of a pulsed laser that incrementally removes material from the composite wall to the desired depth to form the exit orifice.

One aspect of the present invention is the formation of a seal in the area of the exit orifice between the barrier layer 18 and the external layer 22 that prevents expandable layer 20 from leaching out of the system during delivery of the liquid, active agent formulation. In a presently preferred embodiment, exit orifice 24 is drilled and the exposed portion of layer 20 is sealed by barrier layer 18 which because of its rubbery, elastic-like characteristics, flows outwardly about the inner surface of exit orifice 24 during and/or after the formation of the exit orifice 24. In that manner, barrier layer 18 effectively seals the area between the expandable layer 20 and external layer 22. This can be seen most clearly in FIG. 10. In order to flow and seal, barrier layer 18 should have a flowable, rubbery-like consistency at the temperature at which the system operation takes place. Materials, such as copolymers of ethyl acrylate and methyl methacrylate, especially Eudragit NE 30D supplied by RohmPharma, Darmstaat, Germany, are preferred. In either case, the dosage form 10 may be prepared by sequentially coating, on the gelatin capsule, a barrier layer, an expandable layer and a semipermeable layer, as described more fully in EXAMPLE 1. Then, exit orifice 24 is drilled to complete formation of dosage form 10.

The seal also may be formed by having the exit orifice 24 formed within a plug. This can best be seen with reference to FIGS. 6–8. In FIG. 8A, a gelatin capsule 12 (in half-section for ease of illustration) has been coated with the external composite wall 22. The inner barrier layer 18 and expandable layer 20 are not shown. A hole 23 is drilled into the composite wall 22 extending to the external surface of gelatin capsule 12, as seen in FIG. 8B.

Next a plug 26 is formed in hole 23 by adding a liquid polymer that can be cured by heat, radiation or the like. This can best be seen in FIG. 8C. Suitable polymers include polycarbonate bonding adhesives and the like, such as, for example, Loctite® 3201, Loctite® 3211, Loctite® 3321 and Loctite® 3301, sold by the Loctite Corporation, Hartford, Conn. Finally, an exit orifice 24 is drilled into plug 26. Exit orifice 24 extends through plug 26 to expose a portion of the gelatin capsule 12.

Figure 6:
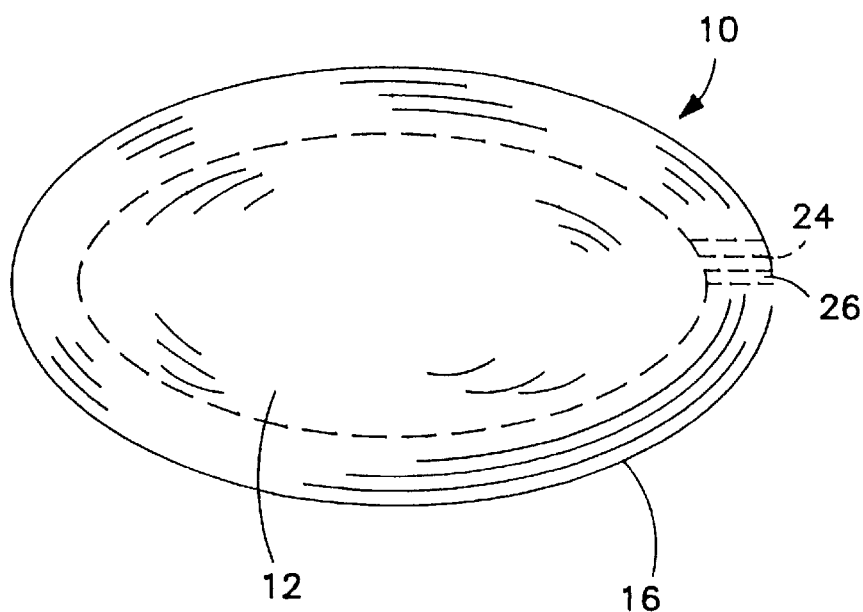
FIG. 6 is an overall view of another embodiment of the dosage form of the invention wherein the exit orifice is formed in a plug seal formed in one end of the dosage form.
Figure 7:
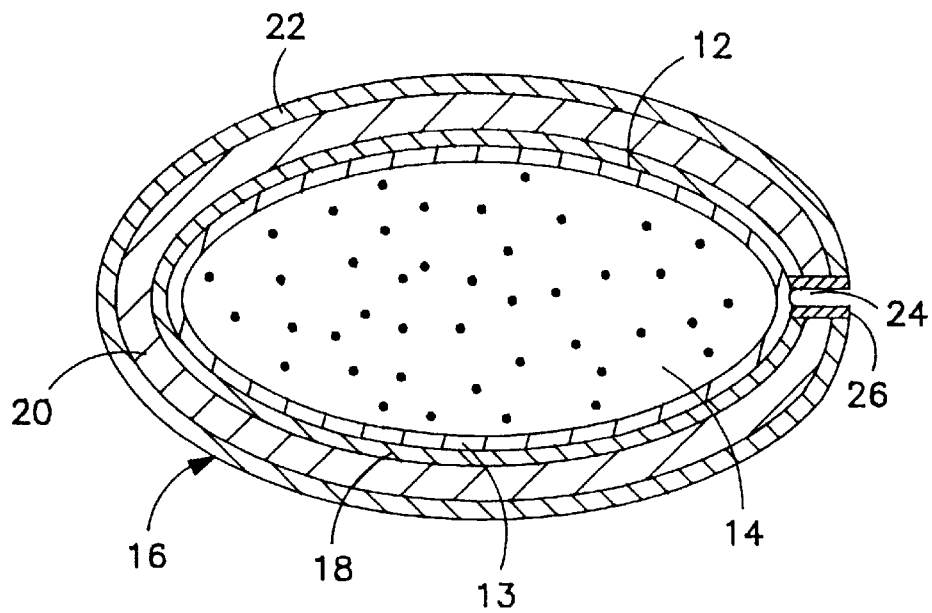
FIG. 7 is an opened view of the dosage form of FIG. 6 showing the structure of the plug seal in greater detail.
Figure 8:
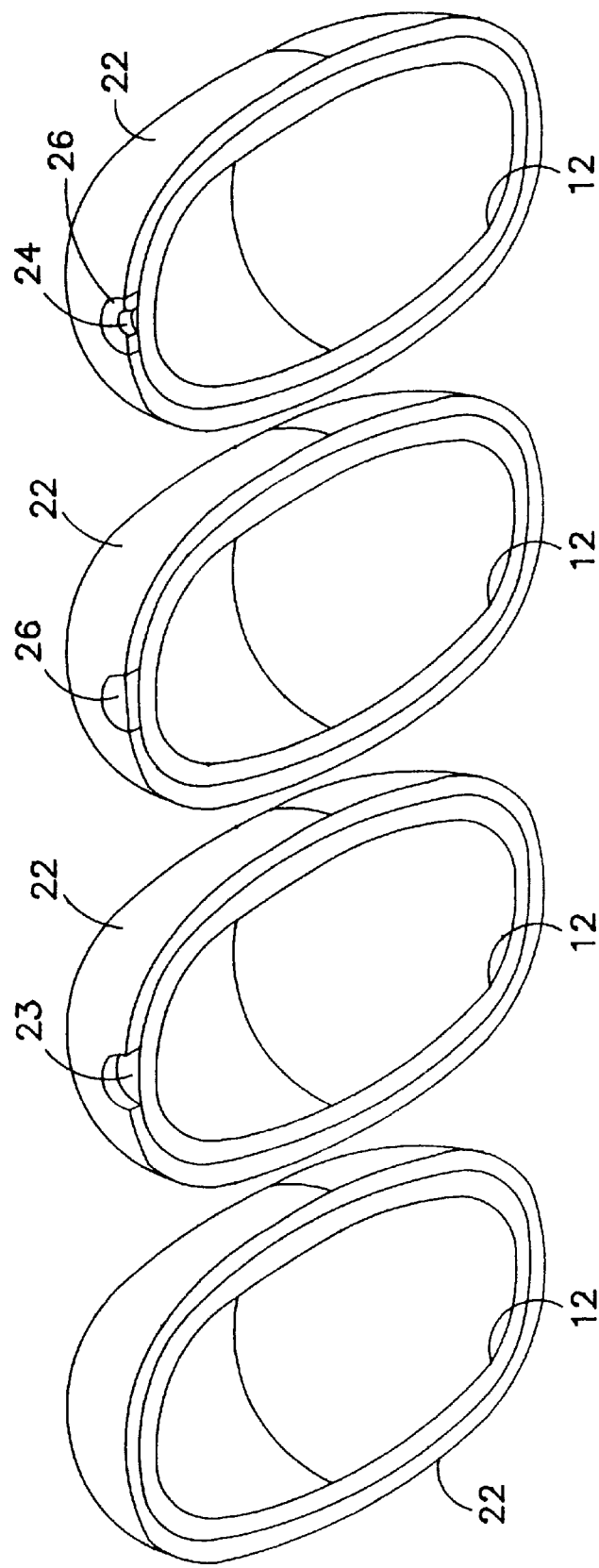
FIGS. 8A–8D provide a schematic view illustrating one method of forming the plug and exit orifice in the dosage form.
Figure 9:
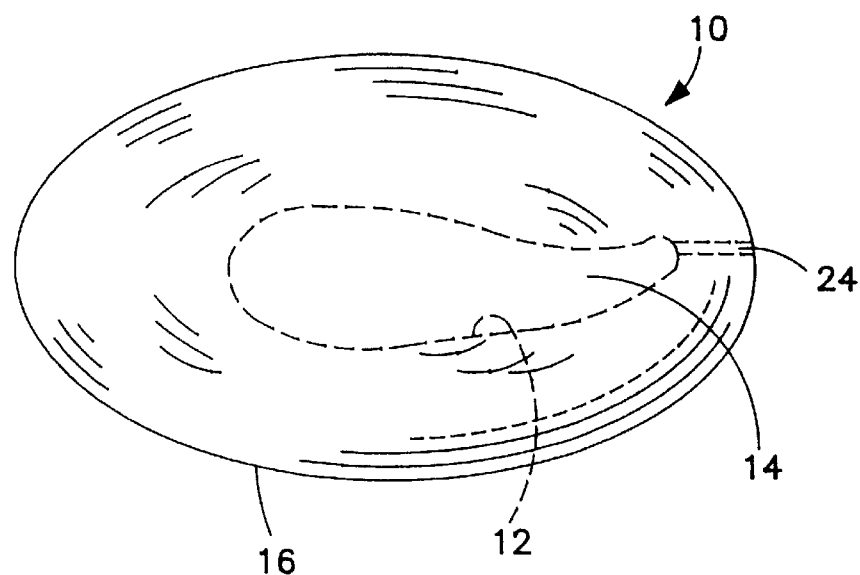
FIG. 9 an overall view of the dosage form after some period of time in the environment of use.
Figure 10:
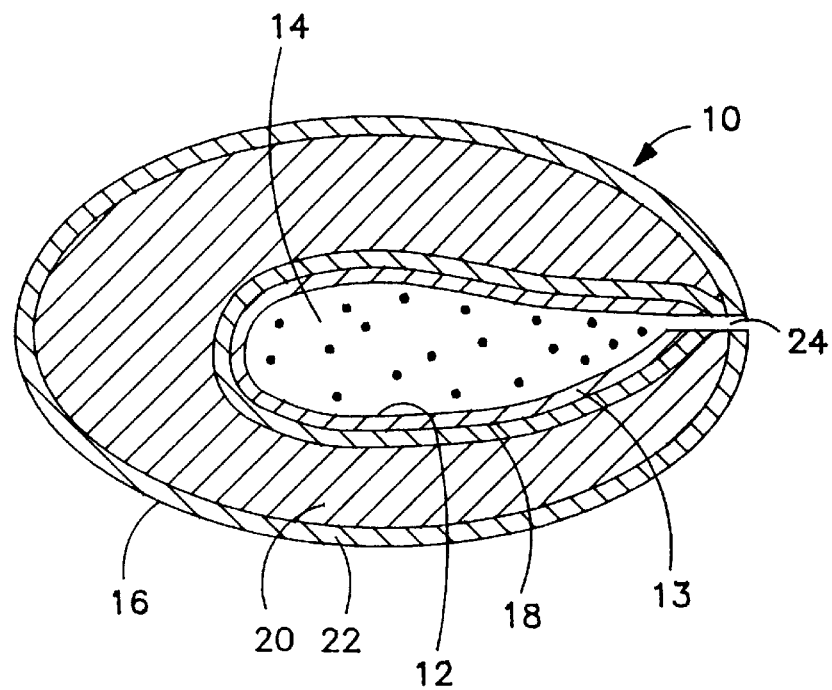
FIG. 10 is an opened view of the dosage form showing the internal structure of the dosage form and the partially collapsed nature of the gelatin capsule and the barrier layer after some period of time in the environment of use.

A completed dosage form having a plug-type seal is illustrated in an overall view of FIG. 6 and in cross-section in FIG. 7.

Figure 3:
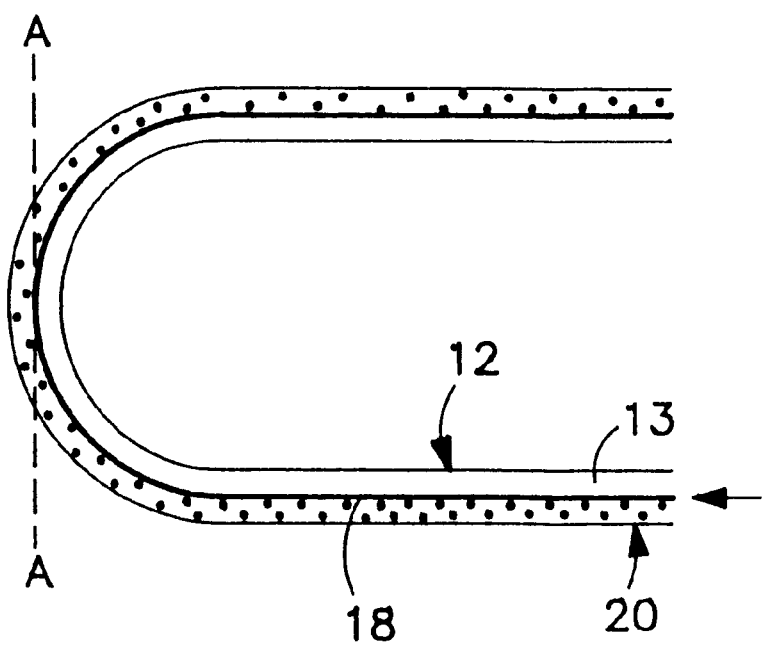
FIG. 3, seen in partial opened view, depicts the dosage form of FIG. 1 at a certain stage of manufacture wherein the gelatin capsule is coated with a barrier layer and an expandable layer.
Figure 4:
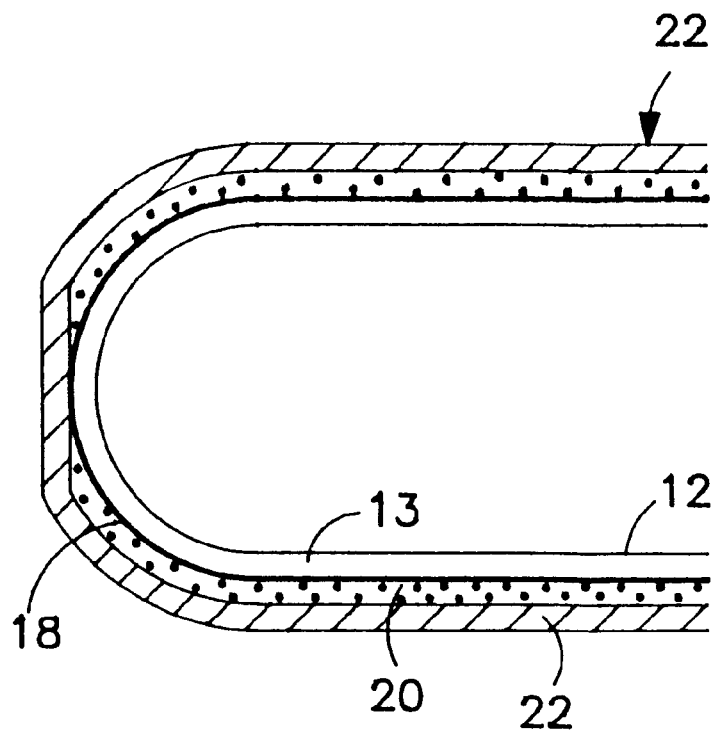
FIG. 4 is a partial opened view of the dosage form of FIG. 3 coated with a semipermeable layer but prior to the formation of an exit orifice.
Figure 5:
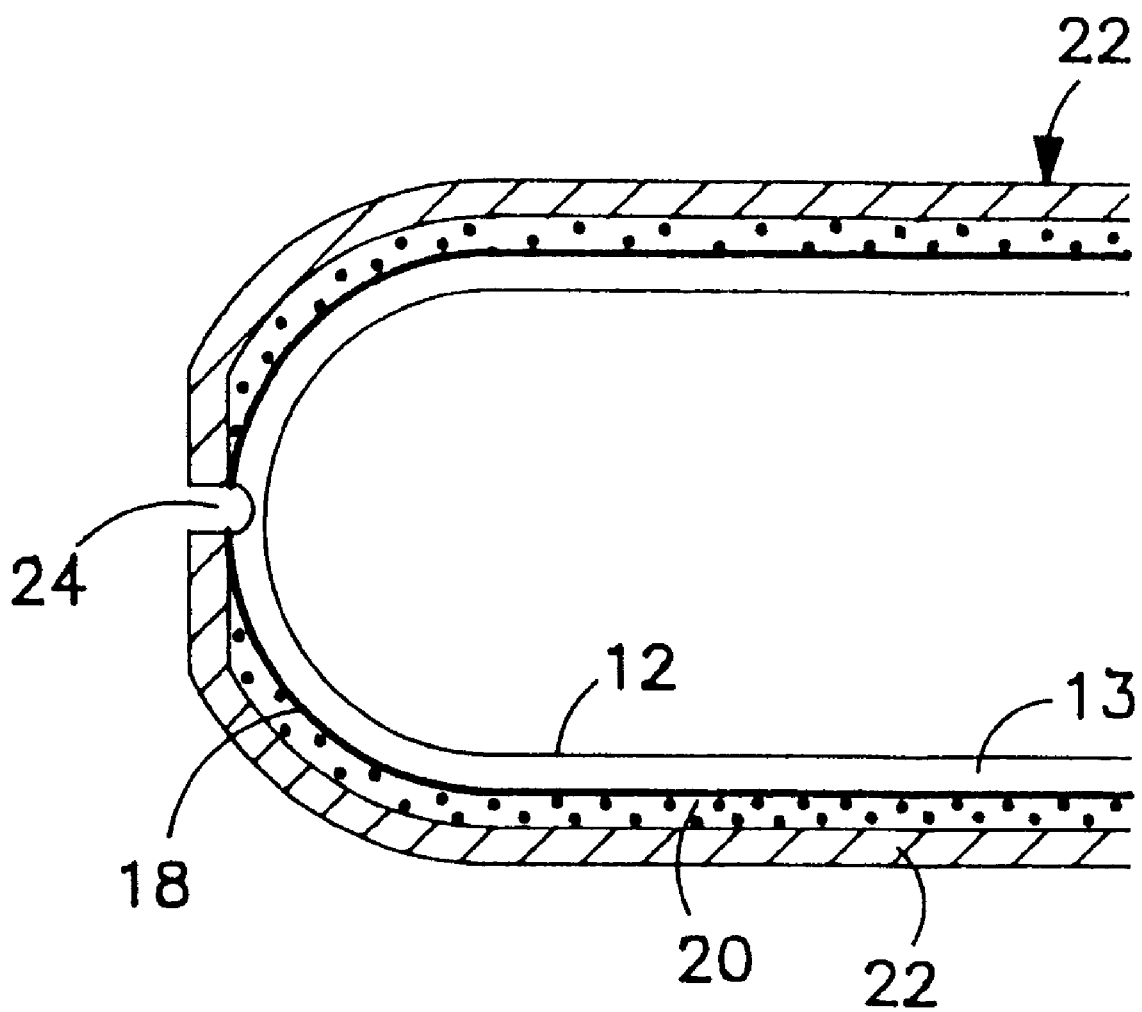
FIG. 5, seen in partial opened view, depicts the dosage form of FIG. 4 in a following sequential stage of manufacture wherein an exit orifice has been formed in one end of the dosage form.

Still another manner of preparing a dosage form having a seal formed on the inner surface of the exit orifice is described with reference to FIGS. 3–5. In FIG. 3, a gelatin capsule 12 (only partially shown) has been coated with he barrier layer 18 and expandable layer 20. Prior to coating with semipermeable layer 22, a section of the expandable layer 20 extending down to, but not through, the barrier layer is removed along line A—A. Then a semipermeable layer 22 is coated onto the dosage form to yield a precursor of the dosage form such as illustrated in FIG. 4. As can be seen from FIG. 4, that portion of the gelatin capsule of the dosage form 10 in the location where the exit orifice is to be formed is covered by the semipermeable layer 22 and the barrier layer 18, but not the expandable layer 20. Consequently, when an exit orifice 24 is formed in that portion of the dosage form 10, as can be seen most clearly in FIG. 5, barrier layer 18 forms a seal at the juncture of external layer 22 and expandable layer 20 such that fluids may pass to expandable layer 20 only through external layer 22. Accordingly, expandable layer 20 is not leached out of the dosage form during operation. The sealing aspect of the invention as described herein and above allows the rate of flow of fluids to the expandable layer 20 to be carefully controlled by controlling the fluid flow characteristics of the semipermeable membrane.

The expression "active agent" as used herein, comprises any active agent, therapeutic compound, or composition that can be delivered from the osmotic system to produce a beneficial and useful result. The term active agent also includes algicide, antioxidant, air purifier, biocide, bactericide, catalyst, chemical reactant, disinfectant, fungicide, fermentation agent, fertility inhibitor, fertility promoter, germicide, plant growth promoter, plant growth inhibitor, preservative, rodenticide, sterilization agent, sex sterilant for insects, and the like.

In the specification and in the accompanying claims, the term active agent also includes active agents for veterinary and human applications, such as pharmaceutical drugs. The term drug includes active substance that produces a desired effect, often beneficial or therapeutic in animals, including warm-blooded mammals, humans and primates; avians; household sport, and farm animals; laboratory animals; fishes; reptiles; and zoo animals. The drug can be in various forms such as unchanged molecules, molecular complexes, pharmacologically acceptable salts such as hydrochloride, hydrobromide, sulfate, laurate, palmitate, phosphate, nitrite, nitrate, borate, acetate, maleate, tartrate, oleate, salicylate, and the like. For acidic drugs, salts of metals, amines, or organic cations, for example quarternary ammonium can be used. Derivatives of drugs, such as bases, ester, ether and amide can be used.

The expression "liquid, active agent formulation" indicates the active agent is present in a composition that is able to flow from the inside of the gelatin capsule to the environment of use as the gelatin capsule us compressed by the action of the expandable layer. The composition may be neat, liquid active agent, or a solution, suspension, slurry, emulsion, self-emulsifying composition, liposomal solution, or other flowable composition in which the active agent is present. The liquid, active agent formulation may be a "solid" at temperatures lower than the temperature of the environment of use, such as body temperature of humans or animals, but the solid should become a flowable, liquid composition after administration or application. The active agent may be accompanied by a binder, antioxidant, pharmaceutically acceptable carrier, permeation enhancer and the like. In those applications wherein the gelatin capsule is highly water soluble, the liquid, active agent formulation will be substantially non-aqueous to maintain the integrity of the gelatin capsule during storage. Formulations of the gelatin wall that are elastic so as to be compressed by the expandable layer and permit efflux of drug from the dosage form but not highly soluble in water may be used with aqueous liquid, active agent formulations.

The amount of an active agent in a dosage form generally is about 0.05 ng to 5 g or more, with individual dosage forms comprising, for example, 25 ng, 1 mg, 5 mg, 10 mg, 25 mg, 100 mg, 250 mg, 500 mg, 750 mg, 1.0 g, 1.2 g, and the like, of active agent depending on the therapeutic application. The dosage systems described herein will usually be administered once, twice or thrice daily, although more frequent dosing and the dosing of multiple units is contemplated for particular therapeutic applications.

The active drug that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synoptic sites, neuroeffector junctional sites, endocrine system, hormone systems, immunological system, organ systems, reproductive system, skeletal system, autocoid systems, alimentary and excretory systems, inhibitory of autocoids and histamine systems, and physiological systems. The active drug that can be delivered for acting on these animal systems includes depressants, beta-blockers, hypnotics, sedatives, psychic energizers, tranquilizers, anticonvulsants, muscle relaxants, steroids, antiparkinson agents, analgesics, anti-inflammatories, polypeptides, local anesthetics, muscle contractants, anti-microbials, anti-malarials, hormonal agents, contraceptives, sympathomimetics, diuretics, anti-parasitics, antineoplastics, hypoglycemics, ophthalmics, electrolytes, diagnostic agents, cardiovascular drugs, calcium channel blockers, angiotensin-converting enzyme inhibitors, protease inhibitors, nucleoside reverse transcriptase inhibitors, antipsychotherapeutic agents, topoisomerase inhibitors, and the like.

Exemplary drugs that can be delivered by the osmotic system of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproternol sulfate, methamphetamine hydrochloride, phenmetrazine hydrochloride, bethanechol chloride, metacholine chloride, pilocarpine hydrochloride, atropine sulfate, methascopolamine bromide, isopropamide iodide, tridihexethyl chloride, phenformin hydrochloride, methylphenidate hydrochloride, oxprenolol hydrochloride, metroprolol tartrate, cimetidine hydrochloride, diphenidol, meclizine hydrochloride, prochlorperazine maleate, phenoxybenzamine, thiethylperazine, maleate, anisindone, diphenadione erythrityl teranitrate, digoxin, isofurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, estrogenic progrestational, corticosteroids, hydrocortisone, hydrocorticosterone acetate, cortisone acetate, triamcinolone, methyltesterone, 17 β-estradiol, ethinyl estradiol, ethinyl estradiol 3-methyl ether, prednisolone, 17-hydroxyprogesterone acetate, 19-nor-progesterone, norgestrel orethindone, norethiderone, progesterone, norgestrone, norethynodrel, aspirin, indomethacin, naproxen, fenoprofen, sulindac, diclofenac, indoprofen, nitroglycerin, propranolol, metroprolol, sodium valproate, valproic acid, taxanes such as paclitaxel, camptothecins such as 9-aminocamptothecin, oxprenolol, timolol, atenolol, alprenolol, cimetidine, clonidine, imipramine, levodopa, chloropropmazine, resperine, methyldopa, dihydroxyphenylalanine, pivaloyloxyethyl ester of α-methyldopa hydrochloride, theophylline, calcium gluconate ferrous lactate, ketoprofen, ibuprofen, cephalexin, haloperiodol, zomepirac, vincamine, diazepam, phenoxybenzamine, β-blocking agents, calcium-channel blocking drugs such as nifedipine, diltiazen, verapamil, lisinopril, captopril, ramipril, fosimopril, benazepril, libenzapril, cilazapril cilazaprilat, perindopril, zofenopril, enalapril, indalapril, qumapril, and the like. Other active agents are known to the dispensing art as described in *Pharmaceutical Sciences*, by Remington, 14th Ed., 1979, published by Mack Publishing Co., Easton, Pa.; *The Drug, The Nurse, The Patient, Including Current Drug Handbook*, 1976, by Falconer et al., published by Saunder Company, Philadelphia, Pa.; *Medical Chemistry*, 3rd Ed., Vol. 1 and 2, by Burger, published by Wiley-Interscience, New York; and, *Physician's Desk Reference*, 55nd Ed., 1998, published by Medical Economics Co., New Jersey.

The method of this invention may be applied generally to commercially available gelatin capsules containing liquid, active agent formulations. The invention has particular application to immediate-release gelatin encapsulated liquid, active agent formulations that are conventionally manufactured and sold, but may be converted into controlled release dosage forms in accordance with this invention.

Examples of commercially available encapsulated liquid formulations that may be converted to controlled release capsules in accordance with the invention include, inter alia, Depakene® brand of valproic acid, Accutane® brand of isotretinoin, Placidyl® brand of ethchlorvynol, Adalat® brand of nifedipine, VePesid® brand of etoposide, Lanoxicaps® brand of digoxin, Zantac® brand of ranitidine hydrochloride, Sandimmune® and Neoral® brands of cyclosporin, Calderol® brand of calcifediol, Zarontin® brand of ethosuximide, Procardia® brand of nifedipine, Rocaltrol® brand of calcitriol and Vescenoid® brand of tretinoin.

Drugs having low water solubility, e.g., less than 50 micrograms/mil, and those having higher molecular weights, e.g., 200 daltons or greater, are deliverable in the dosage forms described herein. The following protease inhibitors and nucleoside reverse transcriptase inhibitors: Crixivan® brand of indinavir sulfate, Epivir® brand of lamivudine, Zerit® brand of stavudine. Viracept® brand of nelfinavir mesylate, Combivir® brand of combination of lamivudine and zidovudine, Invirase® brand of saquinavir mesylate, Norvir® brand of ritonavir, Retrovir® brand of zidovudine, Videx® brand of didanosine, Viramune® brand of nevirapine, Cytovene® brand of ganciclovir, and Hivid® brand of zalcitabine may be prepared as liquid, active agent formulations and delivered in a controlled release manner over a prolonged period of time. The following antipsychotherapeutic agents: Prozac® brand of fluoexetine hydrochloride, Zoloft® brand of sertraline hydrochloride, Paxil® brand of paroxetine hydrochloride, Wellbutrin® brand of bupropion hydrochloride, Serzone® brand of nefazodone hydrochloride, Remeron® brand of mirtazpine, Auroix, Tolvon® brand of mianserin hydrochloride, Elen® brand of zanamivir, Zyprexa® brand of olanzapine, Risperdal® brand of risperidone, Seroquel® brand of quetiapine fumurate, Buspar® brand of buspirone hydrochloride, Xanax® brand of alprazolam, Ativan® brand of lorazepam, Leotan , Tranxene® brand of clorazepate dipotassium, Clozaril® brand of clozapine, Dogmatyl® brand of sulpiride, Solian® brand of amisulpride, Ritalin brand of methylphenidate hydrochloride, and Cylert® brand of pemoline may be prepared as liquid, active agent formulations and delivered by the dosage forms described herein in a controlled release manner over a prolonged period of time.

In many cases, direct use of a liquid form of the active agent is possible. In some cases this may entail the use of the free acid, base, or a salt or ester of an active agent. For dosage forms having application in human and veterinary pharmaceuticals, the salts and esters should be pharmaceutically acceptable and may be selected from the pharmaceutically acceptable salts and esters conventionally used in the pharmaceutical arts. In those and other cases, it may be convenient to use the active agent or its pharmaceutically acceptable salts or esters in conjunction with a liquid pharmaceutically acceptable carrier. Pharmaceutically acceptable carriers useful for mixing with a drug to provide a dispensable formulation, in a presently preferred embodiment, are carriers that are compatible with the gelatin capsule and active agent and which are easily excreted, metabolized, assimilated, or the like by a warm-blooded animal. The carrier medium used for the present purpose can be inorganic, or organic, and of naturally occurring or synthetic origin. Examples of carriers included in the term are substances such as solutions, suspensions, liquids, immiscible liquids, emulsions, sols, colloids, and oils. Representative carriers include liquid alkylene glycols such as ethylene glycol, diethylene glycol, triethylene glycol, ethylene glycol monomethyl ether, liquid polyethylene glycols having a molecular weight of 200, 300, 400 and higher; oils of plant, animal and marine origin such as corn oil, almond oil, babassu oil, eucalyptus oil, cottonseed oil, palm oil, peanut oil, tung oil, mint oil, whale oil, herring oil, mineral oil, and the like: emulsions of castor oil in aqueous solutions of pigskin gelatin: emulsions of gum arabic, water and ethyl cellulose; liquid glyceryl triesters of a low molecular weight fatty acids, particularly medium chain mono-, di-, and tri-gycerides; oils with emulsifiers such as mono-or di-glyceride of a fatty acid; a mixture of from about 70% to about 99.9% propylene glycol and from about 0.1% to 30% of glycerin: a mixture of from about 70% to about 99.9% propylene glycol and from about 0.1 to 30% of ethanol; a mixture by volume of from about 80% to 99.9% of propylene glycol and from about 0.1% to about 20% of a mixture of from about 50% to 99.9% of ethanol or glycerin and from 0.1% to about 50% of sterile water; 5% dextrose in physiological saline; oils mixed with poly-oxyethylene sorbitan monolaurate; a mixture of peanut oil and beeswax; peanut oil containing pectin; glycerine and gelatin, with or without added water; glycerin/castile soap formulation; distilled monoglycerides, distilled propylene glycol monoesters, succinylated monoglycerides, acetylated monoglycerides, glyceryl monostearates, monoglycerides water-in-oil emulsions having a hydrophilic-lipophilic balance of 4, hydrogenated palm oil, hydrogenated palm oil stearine, hydrogenated soybean oil, hydrogenated vegetable oil, hydrogenated cottonseed oil, partially hydrogenated oils, cottonseed oil, sunflower oil, grapeseed oil, and the like.

Dosage form 10 may comprise an antioxidant to slow or effectively stop the rate of any autoxidizable material present in the gelatin capsule. Representative antioxidants comprise a member selected from the group of ascorbic acid; alpha tocopherol; ascorbyl palmitate; ascorbates; isoascorbates; butylated hydroxyanisole; butylated hydroxytoluene; nordihydroguiaretic acid; esters of garlic acid comprising at least 3 carbon atoms comprising a member selected from the group consisting of propyl gallate, octyl gallate, decyl gallate, decyl gallate; 6-ethoxy-2,2,4-trimethyl-1,2-dihydro-guinoline; N-acetyl-2,6-di-t-butyl-p-aminophenol; butyl tyrosine; 3-tertiarybutyl-4-hydroxyanisole; 2-tertiary-butyl-4-hydroxyanisole; 4-chloro-2,6-ditertiary butyl phenol; 2,6-ditertiary butyl p-methoxy phenol; 2,6-ditertiary butyl-p-cresol: polymeric antioxidants; trihydroxybutyro-phenone physiologically acceptable salts of ascorbic acid, erythorbic acid, and ascorbyl acetate; calcium ascorbate; sodium ascorbate; sodium bisulfite; and the like. The amount of antioxidant used for the present purposes is about 0.001% to 25% of the total weight of the composition present in the lumen 15.

Antioxidants are known to the prior art in U.S. Pat. Nos. 2,707,154; 3,573,936; 3,637,772; 4,038,434; 4,186,465 and 4,559,237.

The liquid formulation may also comprise a surfactant or a mixture of surfactants where the surfactant is selected from the group consisting of nonionic, anionic and cationic surfactants. Exemplary nontoxic, nonionic surfactants suitable for forming a composition comprise alkylated aryl polyether alcohols known as Triton®; polyethylene glycol tertdodecyl throether available as Nonic®; fatty and amide condensate or Alrosol®; aromatic polyglycol ether condensate or Neutronyx®; fatty acid alkanolamine or Ninol® sorbitan monolaurate or Span®; polyoxyethylene sorbitan esters or Tweens®; sorbitan monolaurate polyoxyethylene or Tween 20®; sorbitan mono-oleate polyoxyethylene or Tween 80®; polyoxypropylene-polyoxyethylene or Pluronic®; polyglycolyzed glycerides such as Labraosol, polyoxyethylated castor oil such as Cremophor and polyoxypropylene-polyoxyethylene-8500 or Pluronic®. By way of example, anionic surfactants comprise sulfonic acids and the salts of sulfonated esters such as sodium lauryl sulfate, sodium sulfoethyl oleate, dioctyl sodium sulfosuccinate, cetyl sulfate sodium, myristyl sulfate sodium; sulated esters; sulfated amides; sulfated alcohols; sulfated ethers; sulfated carboxylic acids; sulfonated aromatic hydrocarbons; sulfonated ethers; and the like. The cationic surface active agents comprise cetyl pyridinium chloride; cetyl trimethyl ammonium bromide; diethylmethyl cetyl ammonium chloride; benzalkonium chloride; benzethonium chloride; primary alkylamonium salts; secondary alkylamonium salts; tertiary alkylamonium salts; quaternary alkylamonium salts; acylated polyamines; salts of heterocyclic amines; palmitoyl carnitine chloride, behentriamonium methosulfate, and the like. Generally, from 0.01 part to 1000 parts by weight of surfactant, per 100 parts of active agent is admixed with the active agent to provide the active agent formulation. Surfactants are known to the prior art in U.S. Pat. Nos. 2,805, 977; and in 4,182,330.

The liquid formulation may comprise permeation enhancers that facilitate absorption of the active agent in the environment of use. Such enhancers may, for example, open the so-called "tight junctions" in the gastrointestinal tract or modify the effect of cellular components, such a p-glycoprotein and the like. Suitable enhancers include alkali metal salts of salicyclic acid, such as sodium salicylate, caprylic or capric acid, such as sodium caprylate or sodium caprate, and the like. Enhancers may include the bile salts, such as sodium deoxycholate. Various p-glycoprotein modulators are described in U.S. Pat. No. 5,112,817 and 5,643,909, which are incorporated herein by reference. Various other absorption enhancing compounds and materials are described in U.S. Pat. No. 5,824,638, which also is incorporated herein by reference. Enhancers may be used either alone or as mixtures in combination with other enhancers.

The barrier layer 18, expandable layer 20 and semipermeable layer 22 may be applied to the exterior surface of the capsule by conventional coating procedures, e.g. molding, forming, spraying, dipping or the like to form the respective, layer forming composition. The coating procedure is repeated with different layer forming composition to form a laminated or composite wall on the capsule. An air suspension procedure is described in U.S. Pat. No. 2,799,241; *J. Am. Pharm. Assoc.*, Vol. 48, pp. 451–59, 1979; and ibid, Vol. 49, pp. 82–84, 1960. Other standard manufacturing procedures are described in *Modern Plastic Encyclopedia*, Vol. 46, pp. 62–70, 1969; and in *Pharmaceutical Sciences*, by Remington, 18th Ed., Chapter 90, 1990, published by Mack Publishing Co., Easton, Pa.

Exemplary solvents suitable for manufacturing layers comprise inert inorganic and organic solvents that do not adversely harm the materials, the capsule, and the final laminated composite wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglyme, water, aqueous solvents containing inorganic salts such as sodium as acetone and water, acetone and methanol, acetone and ethyl alcohol, methylene dichloride and methanol, and ethylene dichloride and methanol.

The following examples are merely illustrative of the present invention, and they should not be considered as limiting the scope of the invention in any ways, as these examples and other equivalents thereof will become more apparent to those versed in the art in the light of the present disclosure, the drawing figures and the accompanying claims.

EXAMPLE 1

A general procedure for the formation of a composite wall consisting of a barrier layer, an expandable layer and a semipermeable layer formed on soft or hard gelatin capsules is as follows:

A coating solution for the barrier membrane is prepared using cellulose acetate (CA-398-10) and acetyltributylcitrate (ATBC) at a ratio of 4:1 (w/w) dissolved in acetone to make a solution containing 4% solids (w/v). The solution is sprayed at a rate of ~25 g/min onto the soft gelatin capsules or hard gelatin capsules in a pan coating apparatus (e.g. Hi-coater). Typically, for a size O capsule, the weight gain is around 65 mg per capsule.

The expandable layer is formed as an osmotic membrane coating from a coating solution formed as a suspension containing NaCMC (sodium carboxymethylcellulose, 7H4F, MW 700,000), methyl cellulose (A4M), and NaCl at a ratio of approximately 25:8:1 as follows: NaCMC (125 g) and methylcellulose (16 g) are suspended in ethanol (750 g), and NaCl (393) is dissolved in water (2300 g). The salt solution is then added slowly into the ethanol suspension with constant mixing. The above suspension is sprayed onto the barrier coated softgel capsules or hard gelatin capsules at a rate of 15 g/min in a Hi-coater. Typically, a weight gain of around 350 mg per capsule is suitable.

A portion of the osmotic membrane having a size about 150 mil in diameter is removed at the orifice area to expose the barrier membrane. In order to ensure that the inner membrane is not damaged during the removal, a programmable microdrill (e.g. Model #708 sold by Servo Product Company, Pasadena, Calif.) is used with a cone bit having a concave end that is capable of milling the end to about 150 mil in diameter. Then the semipermeable, or rate controlling membrane coating, is applied as follows:

Cellulose acetate (CA398-10) and Pluronic F108 at a ratio around 4:1 (w/w) is dissolved in acetone to make a final solution containing 4% (w/v) solids. That solution is sprayed at a rate of about 25 g/min onto capsules from the previous step in a Hi-coater. The final weight gain is about 85 mg per capsule.

An exit orifice having a size of about 35 mil in diameter is drilled at the orifice area to the external surface of the gelatin capsule using the programmable micro drill as described above with an end mill bit size of about 35 mil in diameter.

EXAMPLE 2

Figure 11:
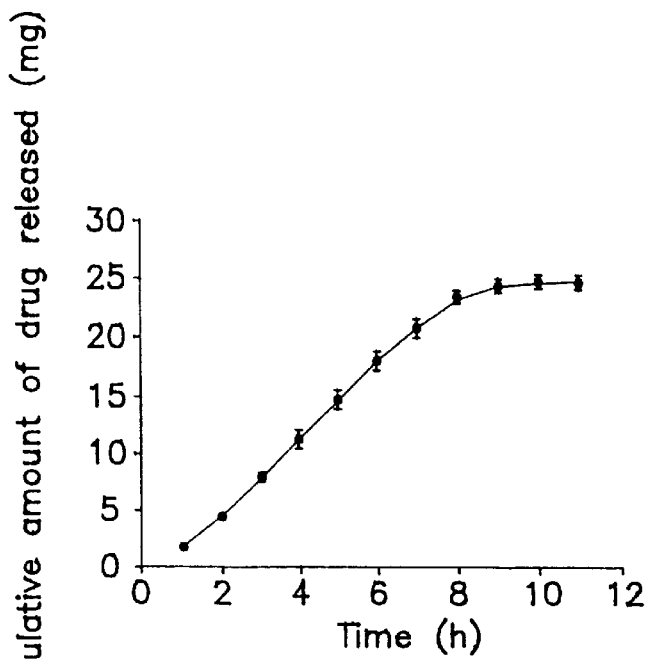
FIG. 11 illustrates the release rate profile of an embodiment of a dosage form of this invention formed from a commercial NEORAL® capsule containing 25 mg of cyclosporin as described in EXAMPLE 2.

The foregoing procedure is used to coat a commercial NEORAL® capsule (Novartis) containing a liquid formulation of cyclosporin (25 mg). The coated capsule is formed with a barrier layer of 25 mg (80% CA 398/20% ATCB), an osmotic layer of 123 mg using the formulation described in EXAMPLE 1, and a semipermeable layer of 127 mg (75% CA 398/25% Pluronic F-108). An orifice of 30 mil is drilled in the end of the dosage form. The release rate profile as determined in a USP bath [paddle assay (paddle speed 50 rpm) and 900 mg AGF (artificial gastric fluid)]. The amount of cyclosporin in the release medium is assayed using HPLC, and the amount of cyclosporin released is shown in FIG. 11. As seen there, the conventional immediate release NEORAL® capsule was converted into a sustained release dosage form releasing cyclosporin over a period of about 10 hours with a substantially zero order rate of release.

EXAMPLE 3

Figure 12:
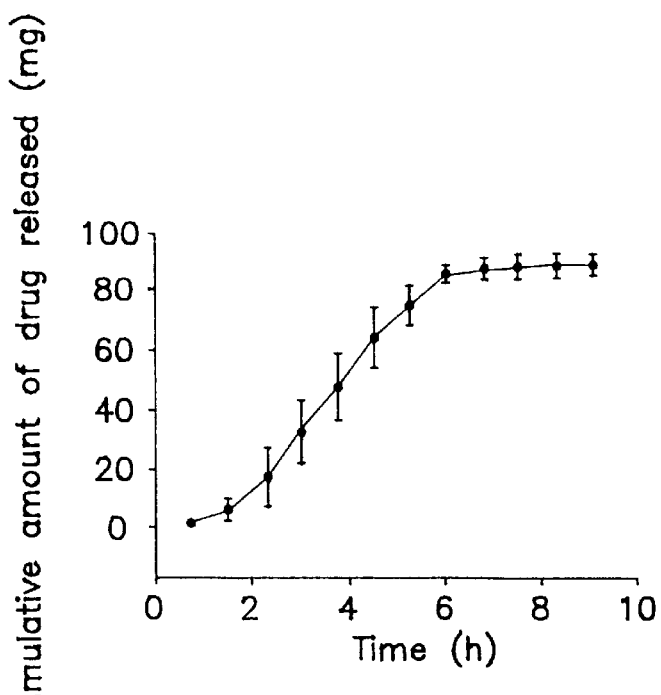
FIG. 12 illustrates the release rate profile of an embodiment of a dosage form of this invention formed from a commercial NEORAL® capsule containing 100 mg of cyclosporin as described in EXAMPLE 3.

A 100 mg NEORAL cyclosporin capsule is coated with 53.5 mg of a barrier layer, 418 mg of an osmotic layer, and 103 mg of a semipermeable layer (all proportions being as described in EXAMPLE 2). The orifice was 35 mils, drilled through the composite wall to approximately the outside wall of the gelatin capsule in one of the ends of the capsule The results of the release rate assay for two such capsules are illustrated in FIG. 12. Cyclosporin is released from the dosage form over a period of time of about 7 hours, with release rate approaching a zero order rate for a period of about 6 hours.

EXAMPLE 4

Figure 13:
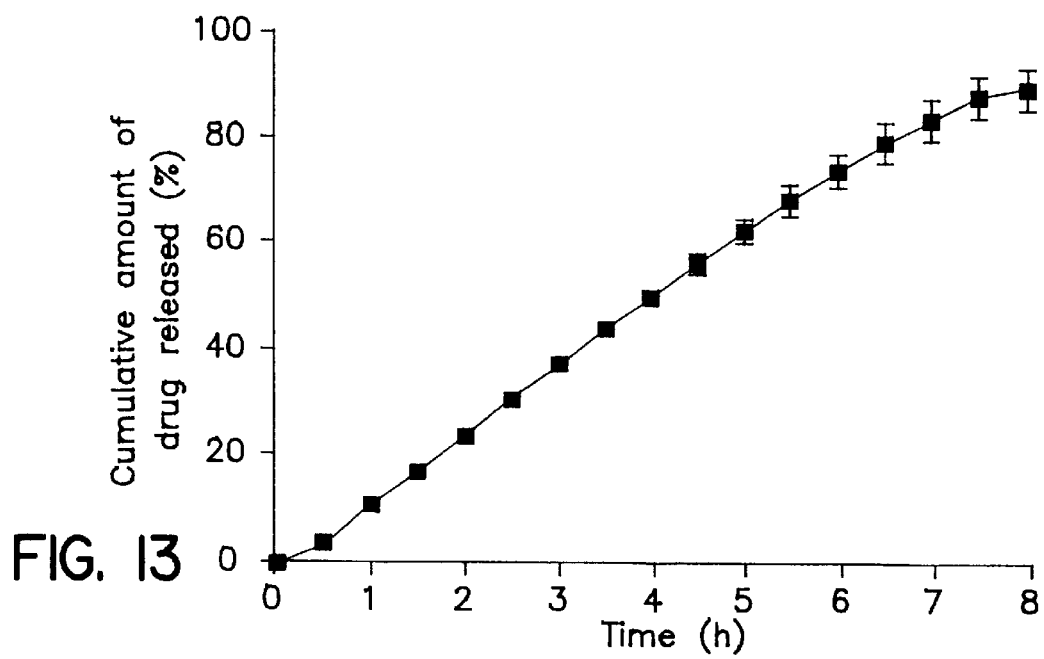
FIG. 13 illustrates the percent release over time of acetaminophen from a dosage form of this invention formed from an acetaminophen soft gelatin capsule containing a liquid formulation of 250 mg of acetaminophen as described in EXAMPLE 4.

Soft gelatin capsules containing 250 mg of acetaminophen (sold as Night-Time Softgels and distributed by Leiner-Health Products, Inc, Carson, Calif. are coated with a 48 mg barrier layer consisting of Eudragit NE 30D:Imwitor (glycerol acetate) (9:1 w/w),and then 400 mg of an osmotic layer consisting of hydroxyethyl cellulose (Natrasol), sodium carboxymethyl cellulose and sodium chloride in a weight ratio of 3:2.9:9.1 is coated on the barrier layer in the manner described in EXAMPLE 1. A 60 mg semipermeable layer having the same materials and proportions as described in EXAMPLE 2 is then coated on the osmotic (expandable) layer. An orifice of 35 mils is drilled through the composite wall to the gelatin capsule wall in one end of the coated capsules as described in EXAMPLE 1. Release of acetaminophen from the capsules was determined in artificial gastric fluid in a shaking bath apparatus as described above. The amount of acetaminophen released as a function of time, normalized for five such systems, is illustrated in FIG. 13.

EXAMPLE 5

Figure 15:
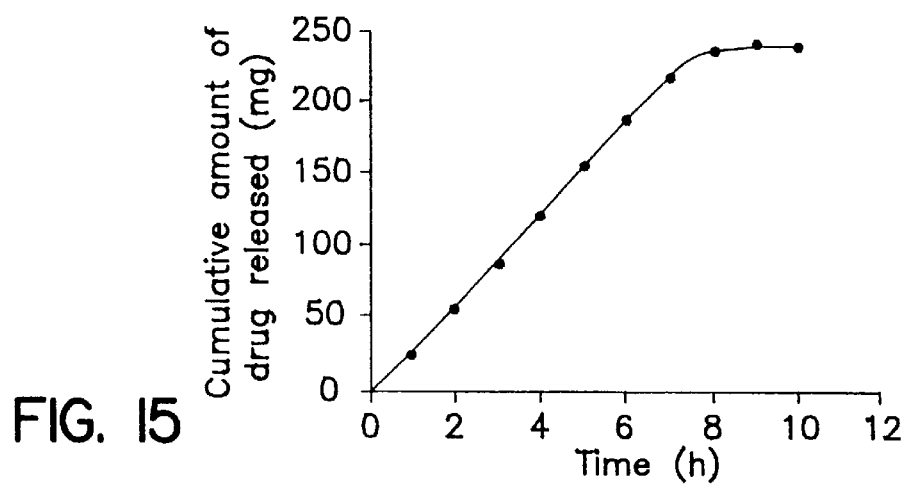
FIG. 15 illustrates the release rate profile of a dosage form of this invention such as illustrated in FIG. 14 and formed from a soft gelatin capsule containing a liquid formulation of 250 mg of acetaminophen as described in EXAMPLE 5.

Soft gelatin capsules containing 250 mg of acetaminophen as identified above (Night-Time Softgels) are coated with 65 mg of a barrier membrane consisting of a mixture of cellulose acetate (CA398-10) and acetyltributyl citrate in a w/w ratio of 8:2. Expandable layers were prepared as concave tablets (350 mg each) from a composition containing 63.3% polyethylene oxide (Polyox 303), 30% sodium chloride, 5% hydroxypropyl cellulose (HPMC-E5), 1% red ferric oxide and 0.25 mg of magnesium stearate. The inner surface of the concave tablets was contacted with a small amount of adhesive and the tablets applied to one side of the capsules in a manner illustrated in FIG. 14B. Then the composite capsule is overcoated with 200 mg of a semipermeable membrane consisting of cellulose acetate (CA398-10) and Pluronic F-108 (75:25 w/w). An exit orifice of 35 mils is drilled through the semipermeable wall and the barrier membrane to the wall of the gelatin capsule wall on the side of the capsule opposite the expandable layer. Release of acetaminophen from capsules prepared as above was determined in a USP bath apparatus in an artificial gastric fluid such as described in EXAMPLE 1 and is illustrated in FIG. 15 for three capsules. The results demonstrate the controlled release of acetaminophen over a period of approximately 8 hours with a substantially zero order release profile.

EXAMPLE 6

Figure 17:
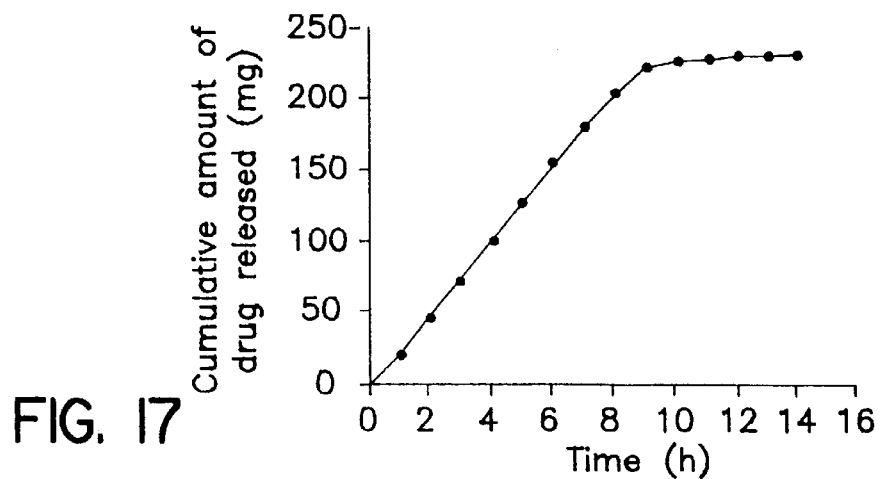
FIG. 17 illustrates the release rate profile of an embodiment of a dosage form of this invention such as illustrated in FIG. 16 and formed from a soft gelatin acetaminophen capsule containing a liquid formulation of 250 mg of acetaminophen as described in EXAMPLE 6.

Coated soft gel capsules containing 250 mg of acetaminophen as identified above (Night-Time Softgels) were prepared in the manner described in EXAMPLE 5, except that the tableted expandable layers were adhesively attached to each end of the capsule, which had been coated with the barrier layer, as illustrated in FIGS. 16A and 16B. Results of the release of acetaminophen are illustrated in FIG. 17 and demonstrate a controlled release of acetaminophen over a period of about 8 hours that is substantially zero order.

EXAMPLE 7

A soft gelatin capsule containing 250 mg of acetaminophen as identified above (Night-Time Softgels) is coated with a barrier layer and expandable, osmotic layer as described in EXAMPLE 4. Before coating the semipermeable membrane, a layer of the osmotic layer is removed to expose the barrier layer, and an amount of polycarbonate bonding adhesive (Loctite 3201) is filled into the space above the exposed barrier layer. Then the adhesive-covered area is exposed to UV light from a UV lamp (UVEX, JH Technologies Inc., or Loctite Corporation) for about 10 seconds to cure the adhesive. A 35 mil hole is drilled through the adhesive/composite wall to the wall of the gelatin capsule as described in EXAMPLE 1. Capsules prepared as above release acetaminophen in a controlled release fashion for a prolonged period of time, e.g., 4–10 hours.

EXAMPLE 8

Figure 18:
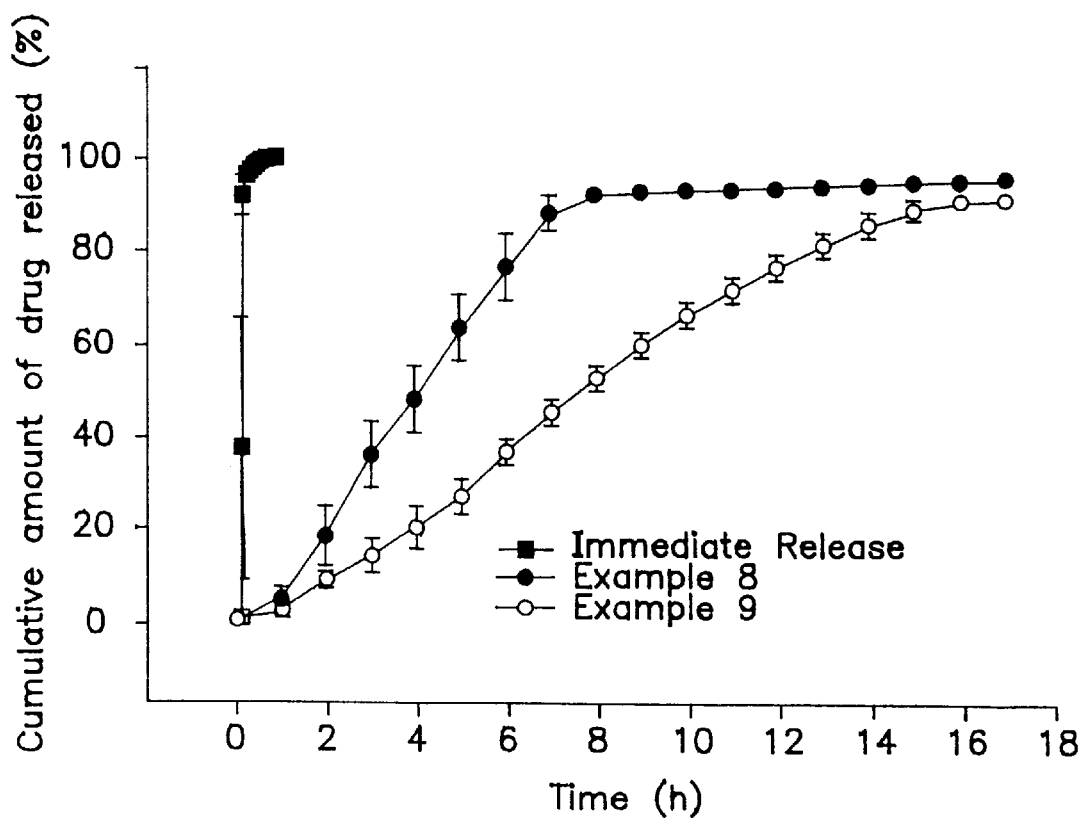
FIG. 18 illustrates the release rate profile of an embodiment of a dosage form of this invention such as illustrated in FIGS. 1 and 2 and formed from a soft gelatin acetaminophen capsule containing a liquid formulation of 250 mg of acetaminophen as described in EXAMPLES 8 and 9, as compared to an immediate release 250 mg acetaminophen capsule.

Soft gelatin capsules containing 250 mg of acetaminophen (sold as Night-Time Softgels and distributed by Leiner-Health Products, Inc, Carson, Calif. are coated with a 48 mg barrier layer consisting of Eudragit NE 30D:Imwitor (glycerol acetate) (80:20 w/w),and then 270 mg of an osmotic layer consisting of hydroxyethyl cellulose (Natrasol), sodium carboxymethyl cellulose and sodium chloride in a weight ratio of 18.8/30.6/50.6 is coated on the barrier layer in the manner described in EXAMPLE 1. A 50 mg semipermeable layer having the same materials and proportions as described in EXAMPLE 2 is then coated on the osmotic (expandable) layer. An orifice of 20 mils is drilled through the composite wall to the gelatin capsule wall in one end of the coated capsules as described in EXAMPLE 1. Release of acetaminophen from the capsules was determined in artificial intestinal fluid using USP II method. The concentration of acetaminophen in the release medium was monitored with a UV spectrometer. The amount of acetaminophen released as a function of time, normalized for three such systems, is illustrated in FIG. 18, along with release data for an immediate release soft gelatin capsule referred to above.

EXAMPLE 9

A delivery system identical to that of Example 8, except for the composition of the semi-permeable membrane, is prepared. In this example, the semipermeable membrane is formed from a mixture of cellulose acetate (CA398-10) and Pluronic F108 at a ratio around 9:1 (w/w) which is dissolved in acetone to make a final solution containing 4% (w/v) solids. An amount of 51 mg of that composition is then coated as a semipermeable layer on the osmotic (expandable) layer. The amount of acetaminophen released as a function of time, normalized for three such systems, is also illustrated in FIG. 18 along with release data for the immediate release soft gelatin capsule referred to in Example 8.

EXAMPLE 10

Several Depakene® soft gelatin capsule (sold by Abbott Laboratories, Abbott Park, Ill.) containing 250 mg of valproic acid are coated in the manner described in Example 8, except that the semipermeable membrane composition is prepared as in Example 9. Exit orifices of 20 mils and 35 mills are drilled in one end of the capsules. The valproic acid is released from the capsules in a controlled release manner over a prolonged period of time when the capsules are tested in a USP bath apparatus as described in Example 1.

The invention comprises the following characteristics and features, either alone or in combination with one or more of each other:

a dosage form comprising (a) a gelatin capsule containing a liquid, active agent formulation; (b) a multilayer wall superposed on the gelatin capsule comprising, in outward order from the capsule: (i) a barrier layer, (ii) an expandable layer, and (iii) a semipermeable layer; and (c) an orifice formed or formable through the wall; a dosage form comprising a gelatin capsule containing a liquid, active agent formulation, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall; the dosage form wherein the expandable layer is hydro-activated; the dosage form wherein the expandable layer is an osmotic layer; the dosage form wherein the barrier layer is impermeable to water; the dosage form wherein the barrier layer is formed as a coating on the gelatin capsule; the dosage form wherein the expandable layer is formed as an osmotic layer coated on the barrier layer; the dosage form wherein the semipermeable layer is formed as a coating on the osmotic layer; the dosage form wherein the barrier layer forms a seal between the expandable layer and the environment at the exit orifice; a method of converting a gelatin capsule containing a liquid active agent formulation into a controlled release dosage form which comprises forming a composite wall on the gelatin capsule by sequentially forming a barrier layer on the external surface of the gelatin capsule, an expandable layer on the barrier layer and a semipermeable layer on the expandable layer; the method wherein at least one of the forming steps comprises a coating step; the method which comprises forming an exit orifice in the wall by sequentially forming an opening in the wall having a diametric dimension greater than the final diameter of the exit orifice and filling the opening with a material in which the exit orifice may be formed; a method of manufacturing a controlled release dosage form comprising a gelatin capsule containing a liquid active agent formulation, which method comprises the steps of (1) forming a barrier layer surrounding the gelatin capsule; (2) forming an expandable layer surrounding the barrier layer-gelatin capsule; (3) removing a portion of the expandable layer in an area in which an exit orifice is to be located without compromising the integrity of the barrier layer in the area; (4) forming a semipermeable layer surrounding the intermediate dosage form prepared through step (4); and forming an exit orifice in the area exposing at least a portion of the gelatin capsule;.a dosage form comprising a gelatin capsule containing a liquid, active agent formulation, the gelatin capsule being surrounded by a barrier layer contacting the external surface of the gelatin capsule, an expandable layer contacting a portion of the barrier layer, a semipermeable layer encompassing at least the expandable layer, and an exit orifice formed or formable in the dosage form extending from the external surface of the gelatin capsule to the environment of use; the dosage form wherein the expandable layer is in one or more discrete sections; the dosage form wherein the expandable layer is in two discrete sections which are applied individually to the respective ends of the capsule; the dosage form wherein the active agent is selected from acetaminophen, cyclosporin, ethchlorvynol, nifedipine, etoposide, digoxin, ranitidine hydrochloride, calcifediol, ethosuximide, calcitriol, paclitaxel, valproic acid, tretinoin isotretinoin, indinavir, lamivudine, stavudine, nelfinavir mesylate, saquinavir mesylate, ritonavir, zidovudine, didanosine, nevirapine, ganciclovir, zalcitabine, fluoexetine, sertraline, paroxetine, bupropion, nefazodone, mirtazpine, mianserin, zanamivir, olanzapine, risperidone, quetiapine fumurate, buspirone, alprazolam, lorazepam, clorazepate dipotassium, clozapine, sulpiride, amisulpride, methylphenidate, pemoline and pharmaceutically-acceptable salts and esters thereof; the dosage form wherein the active agent comprises cyclosporin; the dosage form wherein the active agent comprises acetaminophen; the dosage form wherein the active agent comprises isotretinoin; the dosage form wherein the active agent comprises valproic acid.

Inasmuch as the foregoing specification comprises preferred embodiments of the invention, it is understood that various variations and modifications can be made herein in accordance with the inventive principles disclosed, without departing from the scope of the invention.

What is claimed is:

1. A dosage form comprising (a) a gelatin capsule containing a liquid, active agent formulation; (b) a multilayer wall superposed on the gelatin capsule comprising, in outward order from the capsule: (i) a deformable barrier layer, (ii) an expandable layer, and (iii) a semipermeable layer; and (c) an orifice formed or formable through the wall.

2. The dosage form of claim 1, wherein the expandable layer is hydro-activated.

3. The dosage form of claim 1, wherein the expandable layer is an osmotic layer.

4. The dosage form of claim 2, wherein the deformable barrier layer is impermeable to water.

5. The dosage form of claim 1, wherein the deformable barrier layer is formed as a coating on the gelatin capsule.

6. The dosage form of claim 5, wherein the expandable layer is formed as an osmotic layer coated on the barrier layer.

7. The dosage form of claim 6, wherein the semipermeable layer is formed as a coating on the osmotic layer.

8. A method of converting a gelatin capsule containing a liquid active agent formulation into a controlled release dosage form which comprises forming a composite wall over the gelatin capsule by sequentially forming a deformable barrier layer on the external surface of the gelatin capsule, an expandable layer over the deformable barrier layer and a semipermeable layer over the expandable layer.

9. The method of claim 8, wherein at least one of the forming steps comprises a coating step.

10. The method of claim 8, which comprises forming an exit orifice in the wall by sequentially forming an opening in the wall having a diametric dimension greater than the final diameter of the exit orifice and filling the opening with a material in which the exit orifice may be formed.

11. A method of manufacturing a controlled release dosage form comprising a gelatin capsule containing a liquid active agent formulation, which method comprises the steps of (1) forming a deformable barrier layer surrounding the gelatin capsule; (2) forming an expandable layer surrounding the deformable barrier layer-gelatin capsule; (3) removing a portion of the expandable layer in an area in which an exit orifice is to be located without compromising the integrity of the deformable barrier layer in the area; (4) forming a semipermeable layer surrounding the intermediate dosage form prepared through step (4); and forming an exit orifice in the area exposing at least a portion of the gelatin capsule.

12. The dosage form of claim 1, wherein the deformable barrier layer forms a seal between the expandable layer and the environment at the exit orifice.

13. A dosage form comprising a gelatin capsule containing a liquid, active agent formulation, the gelatin capsule being surrounded by a deformable barrier layer contacting the external surface of the gelatin capsule, an expandable layer contacting at least a portion of the deformable barrier layer, a semipermeable layer surrounding at least the expandable layer, and an exit orifice formed or formable in the dosage form extending from the external surface of the gelatin capsule to the environment of use.

14. The dosage form of claim 13, wherein the expandable layer is in one or more discrete sections.

15. The dosage form of claim 13, wherein the expandable layer is in two discrete sections which are applied individually to the respective ends of the capsule.

16. The dosage form of claim 1, wherein the active agent is selected from the group consisting of acetaminophen, cyclosporin, ethchlorvynol, nifedipine, etoposide, digoxin, ranitidine hydrochloride, calcifediol, ethosuximide, calcitriol, paclitaxel, valproic acid, tretinoin, isotretinoin, indinavir, lamivudine, stavudine, nelfinavir mesylate, saquinavir mesylate, ritonavir, zidovudine, didanosine, nevirapine, ganciclovir, zalcitabine, fluoexetine, sertraline, paroxetine, bupropion, nefazodone, mirtazpine, mianserin, zanamivir, olanzapine, risperidone, quetiapine fumurate, buspirone, alprazolam, lorazepam, clorazepate dipotassium, clozapine, sulpiride, amisulpride, methylphenidate, and pemoline and pharmaceutically-acceptable salts and esters thereof.

17. The dosage form of claim 1, wherein the active agent comprises cyclosporin.

18. The dosage form of claim 1, wherein the active agent comprises acetaminophen.

19. The dosage form of claim 1, wherein the active agent comprises isotretinoin.

20. The dosage form of claim 1, wherein the active agent comprises valproic acid.

* * * * *